United States Patent
Long et al.

(10) Patent No.: US 12,409,072 B2
(45) Date of Patent: Sep. 9, 2025

(54) MULTI-LAYER NEGATIVE PRESSURE INCISIONAL WOUND THERAPY DRESSING

(71) Applicant: KCI Manufacturing Unlimited Company, Athlone (IE)

(72) Inventors: Justin Alexander Long, Lago Vista, TX (US); Christopher Brian Locke, Bournemouth (GB); Timothy Mark Robinson, Shillingstone (GB)

(73) Assignee: KCI Manufacturing Unlimited Company, Westmeath (IE)

( * ) Notice: Subject to any disclaimer, the term of this patent is extended or adjusted under 35 U.S.C. 154(b) by 337 days.

(21) Appl. No.: 17/781,630

(22) PCT Filed: Dec. 4, 2020

(86) PCT No.: PCT/IB2020/061540
§ 371 (c)(1),
(2) Date: Jun. 1, 2022

(87) PCT Pub. No.: WO2021/111412
PCT Pub. Date: Jun. 10, 2021

(65) Prior Publication Data
US 2023/0038460 A1    Feb. 9, 2023

Related U.S. Application Data

(60) Provisional application No. 62/944,031, filed on Dec. 5, 2019.

(51) Int. Cl.
*A61F 13/01* (2024.01)
*A61F 13/00* (2024.01)
(Continued)

(52) U.S. Cl.
CPC ...... *A61F 13/01029* (2024.01); *A61F 13/022* (2013.01); *A61L 15/425* (2013.01);
(Continued)

(58) Field of Classification Search
CPC .......... A61F 13/00068; A61F 13/00029; A61F 13/01029; A61F 13/022; A61F 13/0107;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Japanese Notice of Rejection for Application No. 2021-542412, dated Dec. 5, 2023.

(Continued)

*Primary Examiner* — Marcela I. Shirsat

(57) ABSTRACT

A dressing for treating tissue may be a composite of dressing layers, including a contact layer, a manifold layer, and an adhesive drape. The manifold layer may include one or more layers of felted open-cell foam in some examples. The manifold layer may be relatively thin to reduce the dressing profile and increase flexibility, which can enable it to conform to difficult geometry and other tissue sites under negative pressure. The dressing may have a length and a width less than the length. The manifold layer may include a population of holes extending at least partially therethrough, wherein the holes may be configured to promote anisotropic contraction of the dressing parallel to its width. The population of holes may have a circular, ovoid, triangular, square, hexagonal, irregular, or morphous shape. The dressing may be a bolster that may anisotropically contract to provide a closing force to a linear wound.

19 Claims, 20 Drawing Sheets

(51) Int. Cl.
*A61F 13/02* (2024.01)
*A61F 13/0203* (2024.01)
*A61F 13/0206* (2024.01)
*A61F 13/05* (2024.01)
*A61F 15/00* (2006.01)
*A61L 15/42* (2006.01)
*A61L 15/60* (2006.01)
*A61M 1/00* (2006.01)
*A61M 27/00* (2006.01)

(52) U.S. Cl.
CPC .............. *A61M 1/915* (2021.05); *A61M 1/92* (2021.05); *A61F 13/00063* (2013.01); *A61F 2013/00251* (2013.01); *A61F 2013/00357* (2013.01); *A61F 2013/00536* (2013.01); *A61F 13/01017* (2024.01); *A61F 13/01038* (2024.01); *A61F 13/0206* (2013.01); *A61F 13/0223* (2013.01); *A61F 13/0243* (2013.01); *A61F 13/0283* (2013.01); *A61F 13/0289* (2013.01); *A61F 13/05* (2024.01); *A61F 15/008* (2013.01); *A61L 15/60* (2013.01); *A61M 1/71* (2021.05); *A61M 1/74* (2021.05); *A61M 1/75* (2021.05); *A61M 1/77* (2021.05); *A61M 1/85* (2021.05); *A61M 1/90* (2021.05); *A61M 1/96* (2021.05); *A61M 1/962* (2021.05); *A61M 1/966* (2021.05); *A61M 27/00* (2013.01)

(58) Field of Classification Search
CPC ................ A61F 13/05; A61F 13/00059; A61F 13/01017; A61F 13/01034; A61F 13/01038; A61F 13/0223; A61F 13/0243; A61F 13/0289; A61F 13/00; A61F 13/00063; A61F 13/0206; A61F 13/00055; A61F 13/00995; A61F 2013/00251; A61F 2013/00131; A61F 2013/00136; A61F 2013/00174; A61F 2013/00182; A61F 2013/00246; A61F 2013/0028; A61F 2013/00536; A61F 2013/0054; A61F 2013/00748; A61F 2013/00319; A61F 2013/00357; A61F 2013/00957; A61F 15/008; A61F 13/0283; A61L 15/425; A61L 15/60; A61M 1/008; A61M 1/915; A61M 1/92; A61M 1/75; A61M 1/96; A61M 1/85; A61M 1/71; A61M 1/917; A61M 1/916; A61M 1/918; A61M 1/95; A61M 1/73; A61M 1/966; A61M 1/74; A61M 1/91; A61M 1/962; A61M 1/90; A61M 1/77; A61M 1/912; A61M 2205/3344; A61M 2205/3306; A61M 2205/3317; A61M 2205/3331; A61M 2205/3334; A61M 2205/3368; A61M 2205/6063; A61M 27/00

See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,683,921 A | 8/1972 | Brooks et al. |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,902,565 A | 2/1990 | Brook |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |

(56) References Cited

U.S. PATENT DOCUMENTS

| | | |
|---|---|---|
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,765,123 B2 | 7/2004 | de Jong et al. |
| 6,814,079 B2 | 11/2004 | Heaton et al. |
| 7,381,859 B2 | 6/2008 | Hunt et al. |
| 7,846,141 B2 | 12/2010 | Weston |
| 7,951,124 B2 | 5/2011 | Boehringer et al. |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,168,180 B2 | 10/2015 | Ha et al. |
| 9,198,801 B2 | 12/2015 | Weston |
| 9,211,365 B2 | 12/2015 | Weston |
| 9,289,542 B2 | 3/2016 | Blott et al. |
| 9,421,309 B2 | 8/2016 | Robinson et al. |
| 9,918,733 B2 | 3/2018 | Ingram et al. |
| 9,974,694 B2 | 5/2018 | Locke et al. |
| 10,369,058 B2 | 8/2019 | Ha et al. |
| 10,610,414 B2 | 4/2020 | Hartwell et al. |
| 10,736,788 B2 | 8/2020 | Locke et al. |
| 10,743,900 B2 | 8/2020 | Ingram et al. |
| 11,224,542 B2 | 1/2022 | Robinson et al. |
| 2001/0037118 A1 | 11/2001 | Shadduck |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0161346 A1 | 10/2002 | Lockwood et al. |
| 2004/0030304 A1 | 2/2004 | Hunt et al. |
| 2005/0282895 A1 | 12/2005 | Dosch et al. |
| 2007/0185426 A1 | 8/2007 | Ambrosio et al. |
| 2008/0132819 A1 | 6/2008 | Radl et al. |
| 2008/0177253 A1 | 7/2008 | Boehringer et al. |
| 2008/0275409 A1 | 11/2008 | Kane et al. |
| 2008/0300555 A1 | 12/2008 | Olson et al. |
| 2009/0012482 A1 | 1/2009 | Pinto et al. |
| 2009/0093779 A1 | 4/2009 | Riesinger |
| 2009/0227969 A1 | 9/2009 | Jaeb et al. |
| 2009/0299303 A1 | 12/2009 | Seegert |
| 2010/0063484 A1 | 3/2010 | Heagle |
| 2010/0160871 A1 | 6/2010 | Seegert et al. |
| 2010/0160874 A1 | 6/2010 | Robinson et al. |
| 2010/0160876 A1 | 6/2010 | Robinson et al. |
| 2010/0185163 A1 | 7/2010 | Heagle |
| 2010/0312159 A1 | 12/2010 | Aali et al. |
| 2011/0054422 A1 | 3/2011 | Locke et al. |
| 2011/0087176 A2 | 4/2011 | Blott et al. |
| 2011/0118683 A1 | 5/2011 | Weston |
| 2011/0178451 A1 | 7/2011 | Robinson et al. |
| 2011/0213287 A1 | 9/2011 | Lattimore et al. |
| 2011/0213319 A1 | 9/2011 | Blott et al. |
| 2011/0230809 A1 | 9/2011 | Manwaring et al. |
| 2011/0282309 A1 | 11/2011 | Adie et al. |
| 2011/0301556 A1 | 12/2011 | Lichtenstein |
| 2012/0016334 A1 | 1/2012 | Nakajima et al. |
| 2012/0143113 A1 | 6/2012 | Robinson et al. |
| 2012/0143114 A1 | 6/2012 | Locke et al. |
| 2012/0157945 A1 | 6/2012 | Robinson et al. |
| 2013/0144230 A1 | 6/2013 | Wu et al. |
| 2013/0211349 A1 | 8/2013 | Stokes et al. |
| 2013/0274717 A1 | 10/2013 | Dunn |
| 2014/0066868 A1 | 3/2014 | Freedman et al. |
| 2014/0155791 A1 | 6/2014 | Robinson et al. |
| 2014/0163491 A1 | 6/2014 | Schuessler et al. |
| 2014/0228787 A1 | 8/2014 | Croizat et al. |
| 2014/0236112 A1 | 8/2014 | Von Wolff et al. |
| 2015/0080788 A1 | 3/2015 | Blott et al. |
| 2015/0119832 A1 | 4/2015 | Locke |
| 2015/0174284 A1 | 6/2015 | Payne et al. |
| 2015/0201954 A1 | 7/2015 | Pratt et al. |
| 2015/0320434 A1* | 11/2015 | Ingram ............... A61B 17/32 606/131 |
| 2015/0320602 A1 | 11/2015 | Locke et al. |
| 2015/0320603 A1* | 11/2015 | Locke ............... C07D 403/14 604/543 |
| 2016/0022885 A1 | 1/2016 | Dunn et al. |
| 2016/0038345 A1 | 2/2016 | Ha et al. |
| 2016/0095754 A1 | 4/2016 | Andrews et al. |
| 2016/0158066 A1 | 6/2016 | Chao |
| 2016/0354086 A1 | 12/2016 | Dunn |
| 2017/0007462 A1 | 1/2017 | Hartwell et al. |
| 2017/0135862 A1 | 5/2017 | Tuck et al. |
| 2017/0189237 A1 | 7/2017 | Locke et al. |
| 2017/0197006 A1 | 7/2017 | Johnson et al. |
| 2017/0231822 A1 | 8/2017 | Hoggarth et al. |
| 2017/0239245 A1 | 8/2017 | Hoggarth et al. |
| 2018/0235646 A1* | 8/2018 | Locke ............... A61B 17/32 |
| 2018/0353337 A1 | 12/2018 | Locke |
| 2018/0353338 A1 | 12/2018 | Locke et al. |
| 2018/0353662 A1* | 12/2018 | Locke ............... A61F 13/0206 |
| 2019/0117465 A1 | 4/2019 | Osborne et al. |
| 2019/0192350 A1 | 6/2019 | Gowans et al. |
| 2019/0231944 A1 | 8/2019 | Dunn et al. |
| 2019/0274889 A1 | 9/2019 | Steward et al. |
| 2019/0314209 A1 | 10/2019 | Ha et al. |
| 2020/0046567 A1 | 2/2020 | Carroll et al. |
| 2020/0107965 A1 | 4/2020 | Greener |
| 2020/0146896 A1 | 5/2020 | Rice et al. |
| 2020/0155359 A1 | 5/2020 | Carroll et al. |
| 2020/0383837 A1 | 12/2020 | Gowans et al. |
| 2021/0077302 A1 | 3/2021 | Carroll et al. |
| 2021/0228417 A1 | 7/2021 | Ha et al. |
| 2023/0000687 A1 | 1/2023 | Rice et al. |
| 2023/0000688 A1 | 1/2023 | Rice et al. |
| 2024/0099898 A1 | 3/2024 | Rice et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| DE | 102006017194 A1 | 10/2007 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2098257 A1 | 9/2009 |
| EP | 3263079 A1 | 1/2018 |
| EP | 3378450 A1 | 9/2018 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2365350 A | 2/2002 |
| GB | 2377939 A | 1/2003 |
| JP | S57-013040 A | 1/1982 |
| JP | 4129536 B2 | 8/2008 |
| SG | 71559 | 4/2002 |

(56) References Cited

FOREIGN PATENT DOCUMENTS

| | | |
|---|---|---|
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 0185248 A1 | 11/2001 |
| WO | 2005102234 A2 | 11/2005 |
| WO | 2006114638 A2 | 11/2006 |
| WO | 2008/005532 A2 | 1/2008 |
| WO | 2008136998 A1 | 11/2008 |
| WO | 2009021523 A1 | 2/2009 |
| WO | 2009/146441 A1 | 12/2009 |
| WO | 2010051071 A1 | 5/2010 |
| WO | 2010051073 A1 | 5/2010 |
| WO | 2010075178 A2 | 7/2010 |
| WO | 2011008497 A2 | 1/2011 |
| WO | 2011089098 A1 | 7/2011 |
| WO | 2013/032745 A1 | 3/2013 |
| WO | 2013066426 A2 | 5/2013 |
| WO | 2013071243 A2 | 5/2013 |
| WO | 2013116552 A1 | 8/2013 |
| WO | 2013129343 A1 | 9/2013 |
| WO | 2013149078 A1 | 10/2013 |
| WO | 2014/014922 A1 | 1/2014 |
| WO | 2014014871 A1 | 1/2014 |
| WO | 2014024048 A1 | 2/2014 |
| WO | 2014143487 A1 | 9/2014 |
| WO | 2015172104 A1 | 11/2015 |
| WO | 2015172111 A1 | 11/2015 |
| WO | 2015173547 A1 | 11/2015 |
| WO | 2017195038 A1 | 11/2017 |
| WO | 2018/077872 A1 | 5/2018 |
| WO | 2018/094061 A1 | 5/2018 |
| WO | 2018/226328 A1 | 12/2018 |
| WO | 2019/136164 A1 | 7/2019 |
| WO | 2019152422 A1 | 8/2019 |
| WO | 2020097529 A1 | 5/2020 |

OTHER PUBLICATIONS

European Examination Report for Application No. 20747133.5, dated Dec. 21, 2023.
Office action for related U.S. Appl. No. 16/923,651 dated Feb. 12, 2024.
Japanese Notice of Rejection for Application No. 2019-233695 dated Mar. 5, 2024.
Office action for related U.S. Appl. No. 17/629,174, dated Mar. 26, 2024.
International Search Report and Written Opinion Corresponding to Application No. PCT/IB2020/061540, mailed Feb. 24, 2021.
Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp . 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin

(56) References Cited

OTHER PUBLICATIONS (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax,"Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Partial International Search Report from PCT/US2015/030030 mailed Jul. 22, 2015.
International Search Report and Written Opinion for PCT/US2015/030023 mailed Aug. 24, 2015.
Extended European Search Report for corresponding Application No. 171862527, mailed Nov. 14, 2017.
"Introduction to Polyurethanes: Thermoplastic Polyurethane", American Chemistry Council, 2018, https://polyurethane.americanchemistry.com/polyurethanes/Introduction-to-Polyurethanes/Applications/Thermoplastic-Polyurethane/.
International Search Report and Written Opinion for PCT/US2015/030027 mailed Jul. 15, 2015.
International Search Report and Written Opinion for corresponding Application No. PCT/US2019/027463, mailed Jul. 4, 2019.
Japanese Notice of Rejection for corresponding Application No. 2016-566815, mailed Feb. 5, 2019.
Extended European Search Report for corresponding Application No. 18162504.7, mailed May 24, 2018.
Japanese Notice of Rejection for corresponding Application No. 2016-566785, mailed Jun. 25, 2019.
Japanese Notice of Rejection for corresponding Application No. 2016-566785, mailed Jan. 29, 2019.
Non-Final Office Action for Corresponding U.S. Appl. No. 15/960,310, mailed Apr. 29, 2020.
Japanese Notice of Rejection for Corresponding Application No. 2019-233695, mailed Oct. 13, 2020.
International Search Report and Written Opinion for Corresponding Application No. PCT/US2019/060567, mailed Feb. 14, 2020.
International Search Report and Written Opinion for Corresponding Application No. PCT/US2019/045505, mailed Nov. 7, 2019.
International Search Report and Written Opinion for Corresponding Application No. PCT/US2019/060479, mailed Apr. 7, 2020.
International Search Report and Written Opinion for Corresponding Application No. PCT/US2020/013922, mailed May 4, 2020.
Chinese Notice of Rejection Corresponding to Application No. 2020800099951, mailed Mar. 28, 2022.
International Search Report and Written Opinion for Corresponding Application No. PCT/IB2020/056911, mailed Oct. 21, 2020.
International Search Report and Written Opinion Corresponding to Application No. PCT/IB2020/061435, mailed Mar. 16, 2021.
International Search Report and Written Opinion Corresponding to Application No. PCT/IB2020/061465, mailed Mar. 16, 2021.
Canadian Examination Report for related application 2,947,302, dated Jun. 11, 2021.
Japanese Notice of Rejection for related application 2020-557257, dated Feb. 28, 2023.
Office Action for related U.S. Appl. No. 16/678,450, dated Jul. 31, 2023.
Office Action for related U.S. Appl. No. 16/923,651, dated Aug. 28, 2023.
Office action for related U.S. Appl. No. 16/918,682, dated Sep. 21, 2023.
Japanese Notice of Rejection for Application No. 2021-524440 dated Apr. 16, 2024.
Office action for U.S. Appl. No. 16/678,450, dated Sep. 9, 2024.
Office action for U.S. Appl. No. 16/745,075, dated Jul. 24, 2024.
Japanese Decision of Rejection and Decision for Dismissal of Amendment for Application No. 2021-524440, dated Oct. 15, 2024.
Office action for U.S. Appl. No. 16/918,682, dated Jan. 2, 2025.
Copper Development Association Inc., Introduction to Antimicrobial Copper, Feb. 15, 2024.
Office action for U.S. Appl. No. 17/629,174, dated Feb. 26, 2025.
Office action for U.S. Appl. No. 17/779,755, dated Apr. 9, 2025.
Office action for U.S. Appl. No. 17/779,792, dated Jun. 3, 2025.

\* cited by examiner

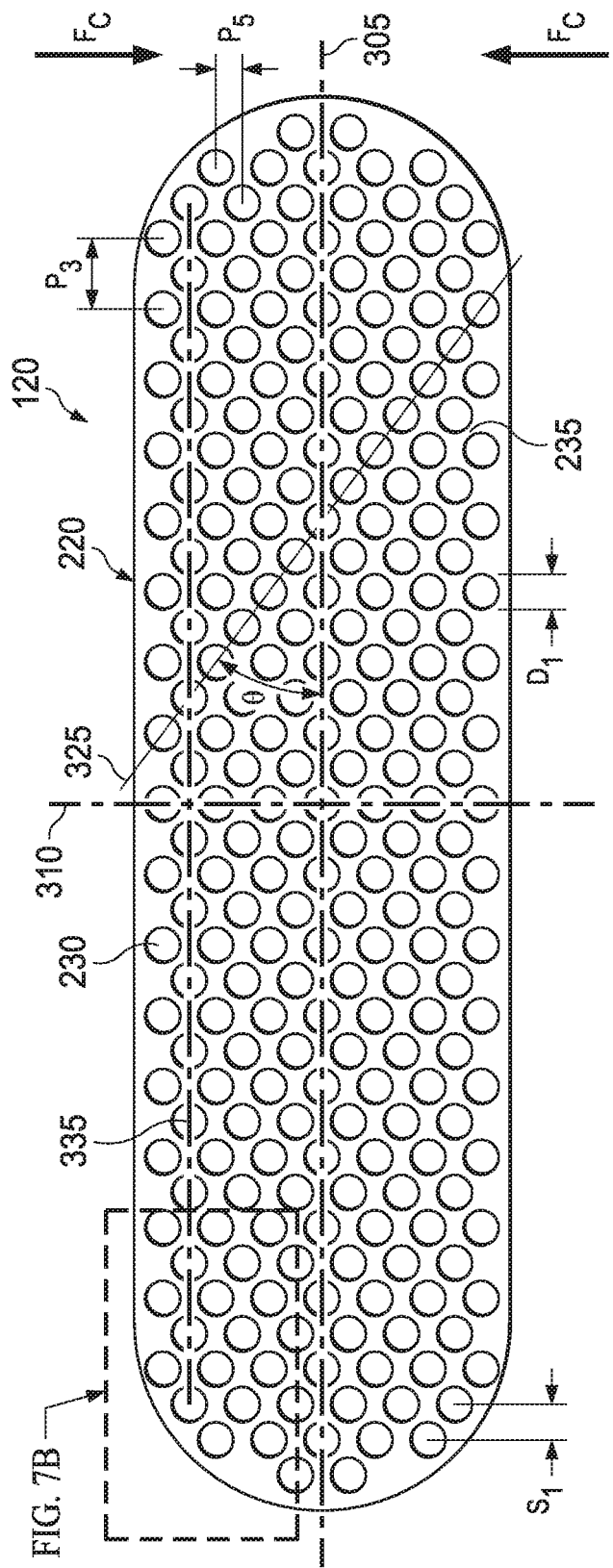

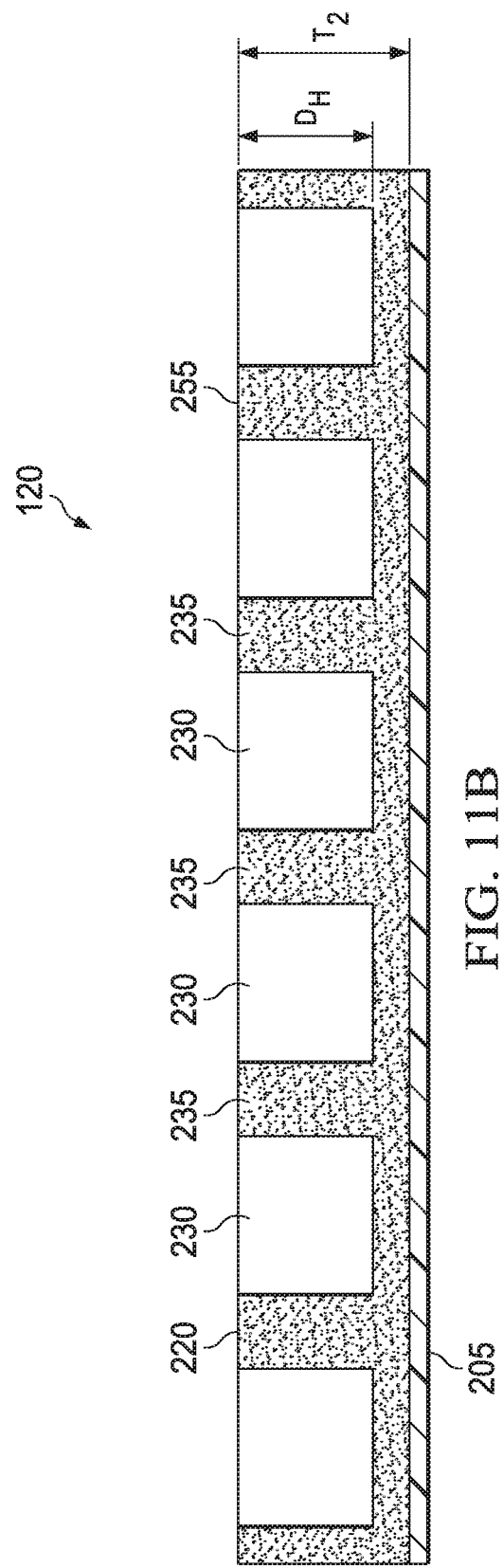

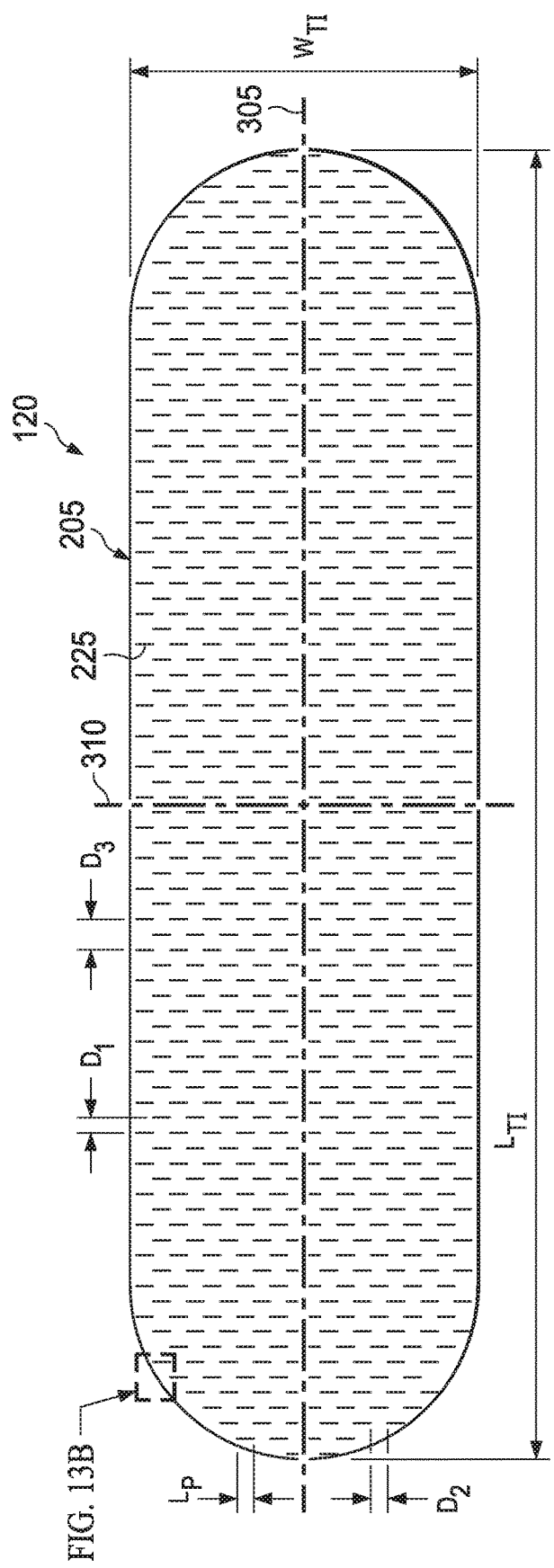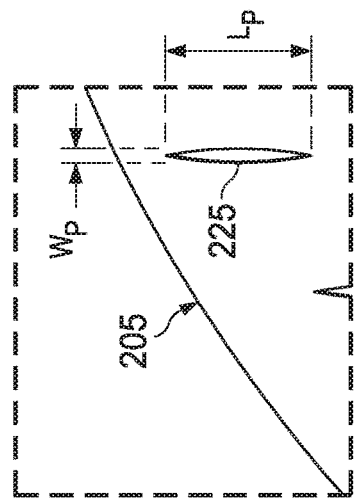
FIG. 13A
FIG. 13B

MULTI-LAYER NEGATIVE PRESSURE INCISIONAL WOUND THERAPY DRESSING

CROSS-REFERENCE TO RELATED APPLICATIONS

This application claims the benefit of priority to U.S. Provisional Application No. 62/944,031, filed on Dec. 5, 2019, which is incorporated herein by reference in its entirety.

TECHNICAL FIELD

The invention set forth in the appended claims relates generally to tissue treatment systems and more particularly, but without limitation, to dressings for tissue treatment and methods of using the dressings for tissue treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a dressing for treating tissue may be a composite of dressing layers, including a contact layer, a manifold layer, and an adhesive drape. The contact layer may include a perforated polymer film in some embodiments. The manifold layer may be multi-layered. The manifold layer may include one or more layers of felted open-cell foam in some examples. The manifold layer may be relatively thin to reduce the dressing profile and increase flexibility, which can enable it to conform to difficult geometry and other tissue sites under negative pressure. The dressing may have a length and a width, wherein the width is less than the length. The manifold layer may include a population of holes extending at least partially through the manifold, wherein the holes may be configured to promote anisotropic contraction of the dressing parallel to the width of the dressing. The population of holes may have a circular, oval, triangular, square, hexagonal, irregular, or amorphous shape. The dressing may be a bolster that may anisotropically contract to provide a closing force to a linear wound.

In some embodiments, the manifold layer may be a felted foam having a firmness factor in a range of about 3 to about 5. In some embodiments, the manifold layer may have a thickness in a range of about 3 millimeters to about 9 millimeters. For example, the manifold layer may have a thickness of about 6 millimeters.

The manifold may be adhered to the polymer film in some embodiments. Suitable bonds between the manifold and the polymer film may include pressure-sensitive adhesive (reactive and non-reactive types); hot melt adhesive (spray applied or deployed as a film, woven, or non-woven); hot press lamination; or flame lamination. The polymer film may also be co-extruded with a bonding layer in-situ, which may be formed from a hot melt adhesive, for example. The dressing may be cut to a desired size before applying the dressing to a tissue. Drape strips or other adhesive strips may be used to seal edges of the dressing and fix the dressing to a patient's skin.

Some embodiments of a dressing for treating a tissue site may include a manifold layer and a contact layer. The manifold layer may include a first side configured to face the tissue site, a second side opposite the first side, and a thickness between the first side and the second side. The manifold layer may further include a plurality of holes extending into the manifold layer on the second side and having a hole depth measured from the second side. The contact layer may be configured to be positioned between the manifold layer and the tissue site. The contact layer may include a plurality of perforations disposed through opposing surfaces of the contact layer.

Some embodiments of a dressing for treating a tissue site with negative pressure may include a contact layer, a first manifold layer coupled to the contact layer, and a second manifold layer coupled to the first manifold layer. The contact layer may be a polymer film including a plurality of perforations through the polymer film. The plurality of perforations may be configured to open. The first manifold layer may be foam having a first density. The second manifold layer may be foam having a second density that is greater than the first density. The second density may be between about 2.6 to about 8.0 lb/ft$^3$. The second manifold layer may include a first surface and a second surface and a plurality of holes extending therebetween. The plurality of holes may be configured to collapse from a relaxed position to a contracted position in response to an application of negative pressure to the dressing.

Some embodiments of a dressing for treating a tissue site with negative pressure may include a contact layer, a first manifold coupled to the contact layer, and a second manifold layer coupled to the first manifold layer. The contact layer may be a polymer film having a plurality of perforations through the polymer film. The first manifold layer may be foam. The second manifold layer be foam having about 120 to about 250 pores per inch, a plurality of holes through the second manifold layer, and a relaxed length and a relaxed width. The relaxed width may be less than the relaxed length. The second manifold layer may be configured to contract to a contracted width in response to an application of negative pressure to the second manifold layer, wherein the contracted width is less than the relaxed width.

Other embodiments of a dressing for treating a tissue site with negative pressure may include a contact layer configured to contact the tissue site, a first manifold coupled to the contact layer, and a second manifold coupled to the first manifold opposite the contact layer. The first manifold may be foam. The second manifold may be foam having a plurality of first regions having a first density and a plurality of second regions having a second density less than the first density.

Other embodiments of a dressing for treating a tissue site with negative pressure may include a tissue interface having a contact layer, a first layer coupled to the contact layer, and a second layer coupled to the first layer. The contact layer may be a polymer film having a plurality of perforations through the polymer film. The second layer may include a plurality of holes through the second layer. The tissue interface may have a first length and a first width, wherein the first width is less than the first length. The tissue interface may be configured to contract to a second width in response to an application of negative pressure to the tissue interface, wherein the second width is less than the first width.

A method for treating a tissue site with negative pressure is also described herein, wherein some example embodiments include applying a tissue interface to the tissue site, wherein the tissue interface may include a contact layer, a first manifold layer coupled to the contact layer, and a second manifold layer coupled to the first manifold layer. The contact layer may be a polymer film having a plurality of perforations through the polymer film. The second manifold layer may include a plurality of holes through the second manifold layer. The tissue interface may have a first length and a first width, and the first width may be less than the first length. The tissue interface may be covered with a cover to form a sealed space containing the tissue interface. A fluid conductor may be fluidly coupling to the tissue interface and to a negative-pressure source. Negative pressure from the negative-pressure source may be applied to the tissue interface through fluid conductor. The tissue interface may contract to a second width in response to an application of negative pressure to the tissue interface, wherein the second width is less than the first width.

Other objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 7A is a top view of another example of a tissue interface that can be associated with some embodiments of the therapy system of FIG. 1;

FIG. 11B is a cross-sectional view of the assembled tissue interface of FIG. 11A along line 11B-11B;

FIG. 13A is a bottom view of an example of a tissue interface that can be associated with some embodiments of the therapy system of FIG. 1;

FIG. 13B is a detail view of the tissue interface taken at reference FIG. 13B in FIG. 13A;

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

Figure 1:
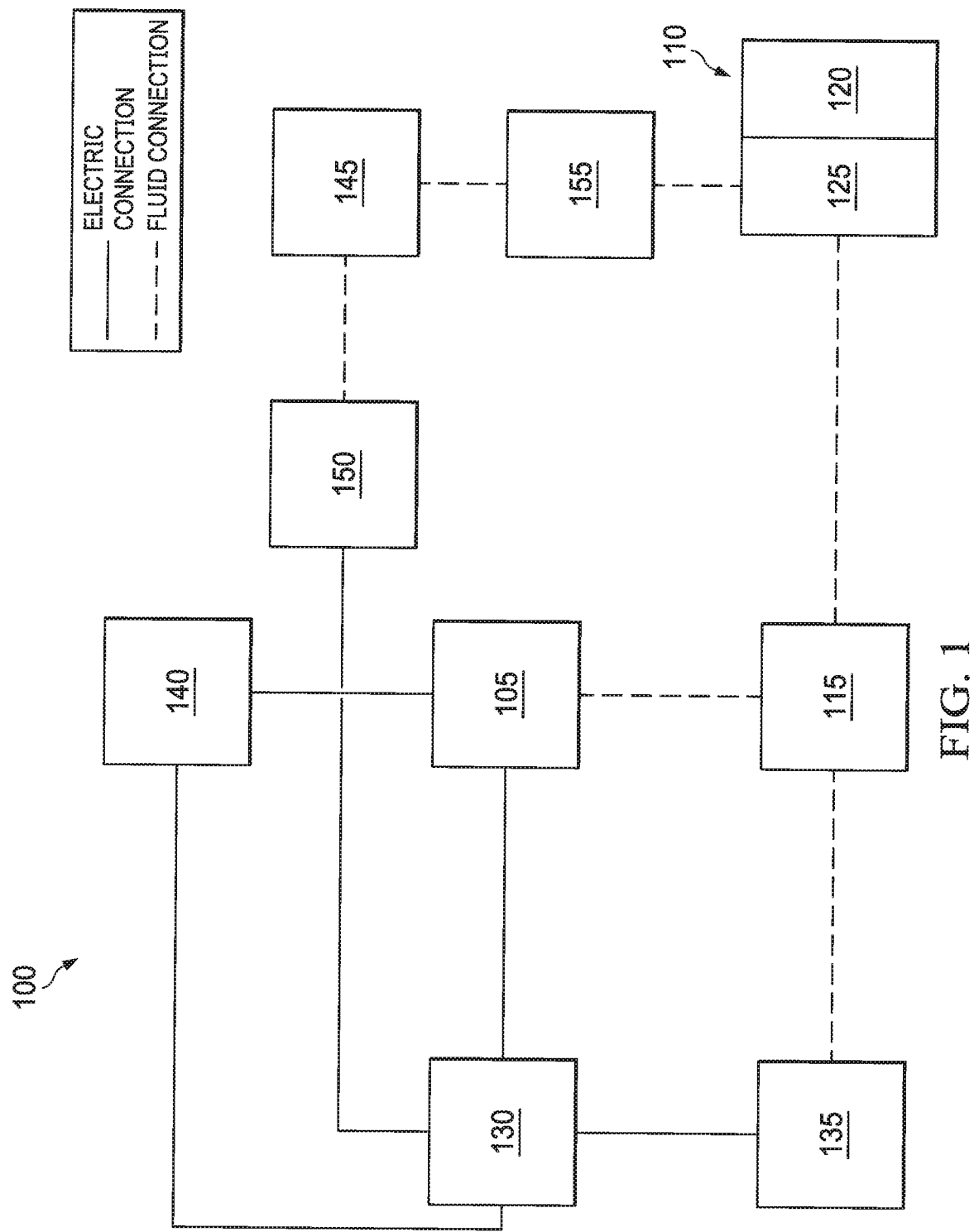
FIG. 1 is a block diagram of an example embodiment of a therapy system that can provide negative-pressure treatment and instillation treatment in accordance with this specification.

FIG. 1 is a block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on a body that is exposed to the external environment, such as an injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may include a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSA-T.R.A.C.™ Pad available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source, such as a positive-pressure source 150, a negative-pressure source such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may include a manifold. A manifold in this context may include a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may be, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may be, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polyamide copolymers. Such materials are commercially available as, for example, Tegaderm® drape, commercially available from 3M Company, Minneapolis Minn.; polyurethane (PU) drape; polyether block polyamide copolymer (PEBAX), for example; and INSPIRE 2301 and INSPIRE 2327 polyurethane films, commercially available from Expopack Advanced Coatings, Wrexham, United Kingdom. In some embodiments, the cover 125 may comprise INSPIRE 2301 having an MVTR (upright cup technique) of 2600 g/m$^2$/24 hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream" may refer to a location in a fluid path relatively closer to a source of negative pressure or further away from a source of positive pressure. Conversely, the term "upstream" may refer to a location further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

In some embodiments, the controller 130 may have a continuous pressure mode, in which the negative-pressure source 105 is operated to provide a constant target negative pressure for the duration of treatment or until manually deactivated. Additionally or alternatively, the controller may have an intermittent pressure mode. For example, the controller 130 can operate the negative-pressure source 105 to cycle between a target pressure and atmospheric pressure. For example, the target pressure may be set at a value of 135 mmHg for a specified period of time (e.g., 5 min), followed by a specified period of time (e.g., 2 min) of deactivation. The cycle can be repeated by activating the negative-pressure source 105, which can form a square wave pattern between the target pressure and atmospheric pressure.

In some example embodiments, the increase in negative-pressure from ambient pressure to the target pressure may not be instantaneous. For example, the negative-pressure source 105 and the dressing 110 may have an initial rise time. The initial rise time may vary depending on the type of dressing and therapy equipment being used. For example, some therapy systems may increase negative pressure at a rate of about 20-30 mmHg/second, and other therapy systems may increase negative pressure at a rate of about 5-10 mmHg/second. If the therapy system 100 is operating in an intermittent mode, the repeating rise time may be a value substantially equal to the initial rise time.

In some example dynamic pressure control modes, the target pressure can vary with time. For example, the target pressure may vary in the form of a triangular waveform, varying between a negative pressure of 50 and 135 mmHg with a rise rate of negative pressure set at a rate of 25 mmHg/min. and a descent rate set at 25 mmHg/min. In other embodiments of the therapy system 100, the triangular waveform may vary between negative pressure of 25 and 135 mmHg with a rise rate of about 30 mmHg/min and a descent rate set at about 30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

In some embodiments, the controller 130 may receive and process data, such as data related to instillation solution provided to the tissue interface 120. Such data may include the type of instillation solution prescribed by a clinician, the volume of fluid or solution to be instilled to a tissue site ("fill volume"), and the amount of time prescribed for leaving solution at a tissue site ("dwell time") before applying a negative pressure to the tissue site. The fill volume may be, for example, between 10 and 500 mL, and the dwell time may be between one second to 30 minutes. The controller 130 may also control the operation of one or more components of the therapy system 100 to instill solution. For example, the controller 130 may manage fluid distributed from the solution source 145 to the tissue interface 120. In some embodiments, fluid may be instilled to a tissue site by applying a negative pressure from the negative-pressure source 105 to reduce the pressure at the tissue site, drawing solution into the tissue interface 120. In some embodiments, solution may be instilled to a tissue site by applying a positive pressure from the positive-pressure source 150 to move solution from the solution source 145 to the tissue interface 120. Additionally or alternatively, the solution source 145 may be elevated to a height sufficient to allow gravity to move solution into the tissue interface 120.

The controller 130 may also control the fluid dynamics of instillation by providing a continuous flow of solution or an intermittent flow of solution. Negative pressure may be applied to provide either continuous flow or intermittent flow of solution. The application of negative pressure may be implemented to provide a continuous pressure mode of operation to achieve a continuous flow rate of instillation solution through the tissue interface 120, or it may be implemented to provide a dynamic pressure mode of operation to vary the flow rate of instillation solution through the tissue interface 120. Alternatively, the application of negative pressure may be implemented to provide an intermittent mode of operation to allow instillation solution to dwell at the tissue interface 120. In an intermittent mode, a specific fill volume and dwell time may be provided depending, for example, on the type of tissue site being treated and the type of dressing being utilized. After or during instillation of solution, negative-pressure treatment may be applied. The controller 130 may be utilized to select a mode of operation and the duration of the negative pressure treatment before commencing another instillation cycle.

Figure 2A:
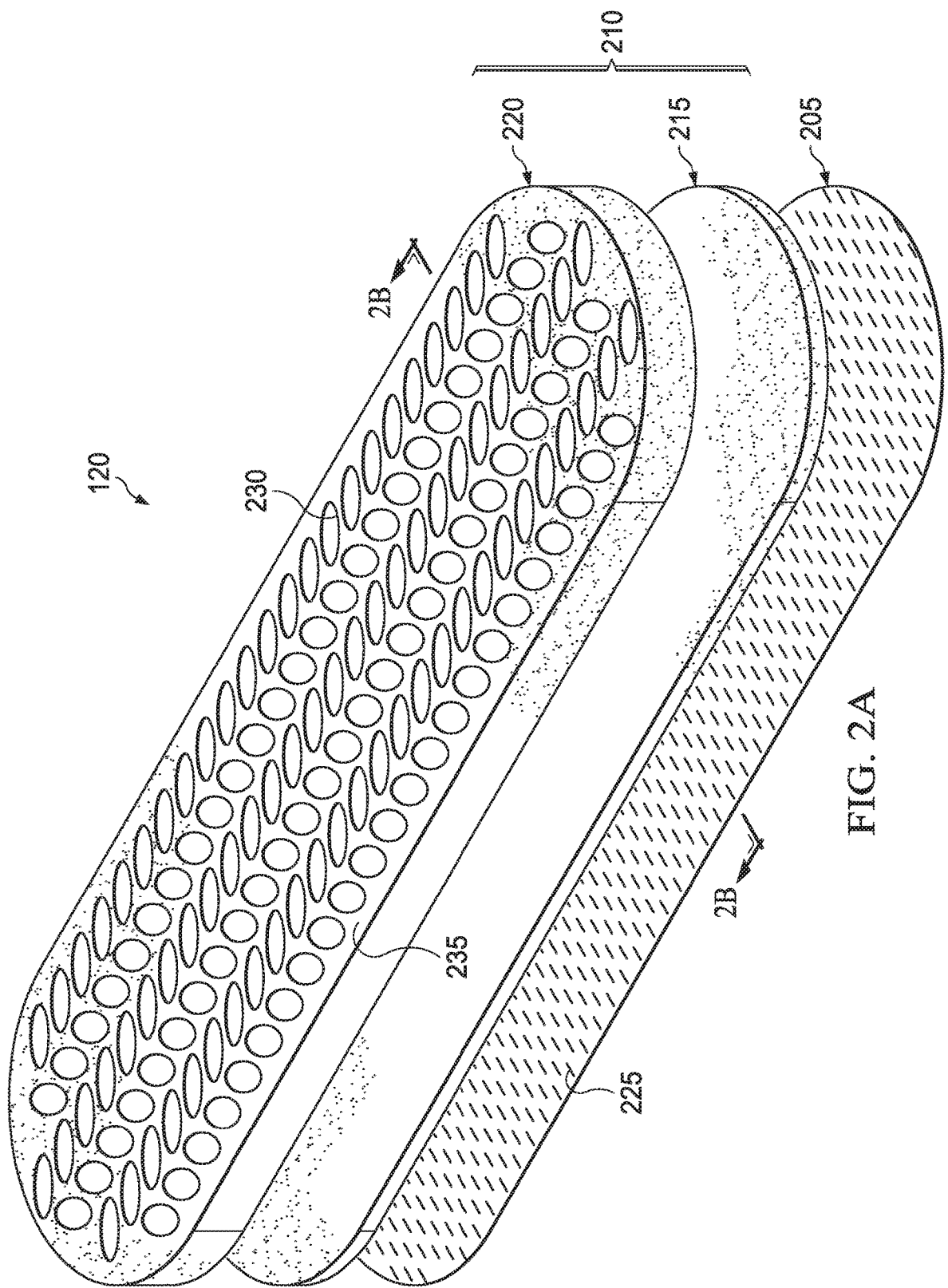
FIG. 2A is an exploded view of an example of a tissue interface that can be associated with some embodiments of the therapy system of FIG. 1.

FIG. 2A is an exploded view of an example of the tissue interface 120 of FIG. 1, illustrating additional details that may be associated with some embodiments in which the tissue interface 120 includes more than one layer. Herein, various examples of the tissue interface 120 are described that may be suitable for use with the dressing 110 and the therapy system 100. Further, features or elements of the tissue interface 120 described herein may be referred to as part of the therapy system 100 or the dressing 110 without reference to the tissue interface 120.

In the example of FIG. 2A, the tissue interface 120 may include a first layer, such as a contact layer 205, and a second layer, such as a manifold layer 210. The manifold layer 210 may include a first manifold layer 215 and a second manifold layer 220. In some embodiments, the contact layer 205 may be disposed adjacent to the manifold layer 210. For example, the contact layer 205 and the manifold layer 210 may be stacked so that the contact layer 205 is in contact with the manifold layer 210. The contact layer 205 may also be heat-bonded or adhered to the manifold layer 210 in some embodiments, for example, using hot melt adhesive. The first manifold layer 215 and the second manifold layer 220 may be stacked so that the first manifold layer 215 is in contact with the second manifold layer 220. The first manifold layer 215 and the second manifold layer 220 may also be heat-bonded or adhered to the manifold layer 210 in some embodiments. In some embodiments, the contact layer 205 optionally includes a low-tack adhesive, which can be configured to hold the tissue interface 120 in place while the cover 125 is applied. The low-tack adhesive may be continuously coated on the contact layer 205 or applied in a pattern.

The contact layer 205 may include a means for controlling or managing fluid flow. In some embodiments, the contact layer 205 may be a fluid control layer comprising a liquid-impermeable, elastomeric material. For example, the contact layer 205 may be a polymer film, such as a polyurethane film. In some embodiments, the contact layer 205 may be the same material as the cover 125. The contact layer 205 may also have a smooth or matte surface texture in some embodiments. A glossy or shiny finish finer or equal to a grade B3 according to the SPI (Society of the Plastics Industry) standards may be particularly advantageous for some applications. In some embodiments, variations in surface height may be limited to acceptable tolerances. For example, the surface of the contact layer 205 may have a substantially flat surface, with height variations limited to 0.2 millimeters over a centimeter.

In some embodiments, the contact layer 205 may be hydrophobic. The hydrophobicity of the contact layer 205 may vary, but may have a contact angle with water of at least ninety degrees in some embodiments. In some embodiments the contact layer 205 may have a contact angle with water of no more than 150 degrees. For example, in some embodiments, the contact angle of the contact layer 205 may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTÅ125, FTÅ200, FTÅ2000, and FTÅ4000 systems, all commercially available from First Ten Angstroms, Inc., of Portsmouth, VA, and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles herein represent averages of 5-9 measured values, discarding both the highest and lowest measured values. The hydrophobicity of the contact layer 205 may be further enhanced with a hydrophobic coating of other materials, such as silicones and fluorocarbons, either as coated from a liquid, or plasma coated.

The contact layer 205 may also be suitable for welding to other layers, including the manifold layer 210. For example, the contact layer 205 may be adapted for welding to polyurethane foams using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials, such as polyethylene. In some embodiments, the manifold layer 210 may be flame laminated to the manifold layer 210.

The area density of the contact layer 205 may vary according to a prescribed therapy or application. In some embodiments, an area density of less than 40 grams per square meter may be suitable, and an area density of about 20-30 grams per square meter may be particularly advantageous for some applications.

In some embodiments, for example, the contact layer 205 may be a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styreneics, silicones, fluoropolymers, and acetates. A thickness between 20 microns and 100 microns may be suitable for many applications. Films may be clear, colored, or printed. More polar films suitable for laminating to a polyethylene film include polyamide, copolyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

The contact layer 205 may have one or more passages, which can be distributed uniformly or randomly across the contact layer 205. In some embodiments, the passages may be bi-directional and pressure-responsive. For example, each of the passages generally may be an elastic passage that is normally unstrained to substantially reduce liquid flow, and can expand or open in response to a pressure gradient and/or in response to the contraction of the manifold layer 210. As illustrated in the example of FIG. 2A, the passages may be perforations 225 in the contact layer 205. Perforations 225 may be formed by removing material from the contact layer 205. For example, perforations 225 may be formed by cutting through the contact layer 205. In the absence of a pressure gradient across the perforations 225, the perforations 225 may be sufficiently small to form a seal or fluid restriction, which can substantially reduce or prevent liquid flow. Additionally, or alternatively, one or more of the passages may be or may function as an elastomeric valve that is normally closed when unstrained to substantially prevent liquid flow, and can open in response to a pressure gradient and/or in response to the contraction of the manifold layer 210. In some examples, the passages may be fenestrations in the contact layer 205. Generally, fenestrations are a species of perforation, and may also be formed by removing material from the contact layer 205. The amount of material removed and the resulting dimensions of the fenestrations may be up to an order of magnitude less than perforations.

In some embodiments, the perforations 225 may be formed as slots (or fenestrations formed as slits) in the contact layer 205. In some examples, the perforations 225 may be linear slots having a length less than 4 millimeters and a width less than 1 millimeter. The length may be at least 2 millimeters, and the width may be at least 0.4 millimeters in some embodiments. A length of about 3 millimeters and a width of about 0.8 millimeters may be particularly suitable for many applications, and a tolerance of about 0.1 millimeter may also be acceptable. Such dimensions and tolerances may be achieved with a laser cutter, for example. Slots of such configurations may function as imperfect elastomeric valves that can substantially reduce liquid flow in a normally closed or resting state. For example, such slots may form a flow restriction without being completely closed or sealed. The slots can expand or open wider in response to a pressure gradient and/or in response to the contraction of the manifold layer 210 to allow increased liquid flow.

The manifold layer 210 generally includes a manifold or a manifold layer, which can provide a means for collecting or distributing fluid across the tissue interface 120 under pressure. For example, the manifold layer 210 may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as from a source of instillation solution, across the tissue interface 120.

In some illustrative embodiments, the pathways of the manifold layer 210 may be interconnected to improve distribution or collection of fluids. In some illustrative embodiments, the manifold layer 210 may be a porous material having interconnected fluid pathways. Examples of suitable porous material that comprise or can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, the manifold layer 210 may additionally or alternatively include projections that form interconnected fluid pathways. For example, the manifold layer 210 may be molded to provide surface projections that define interconnected fluid pathways.

In some embodiments, the manifold layer 210 may be a reticulated foam having pore sizes and free volume that may vary according to needs of a prescribed therapy. For example, a reticulated foam having a free volume of at least 90% may be suitable for many therapy applications, and a foam having an average pore size in a range of 400-600 microns may be particularly suitable for some types of therapy. The tensile strength of the manifold layer 210 may also vary according to needs of a prescribed therapy. For example, the tensile strength of a foam may be increased for instillation of topical treatment solutions. The 25% compression load deflection of the manifold layer 210 may be at least 0.35 pounds per square inch, and the 65% compression load deflection may be at least 0.43 pounds per square inch. In some embodiments, the tensile strength of the manifold layer 210 may be at least 10 pounds per square inch. The manifold layer 210 may have a tear strength of at least 2.5 pounds per inch. In some embodiments, the manifold layer 210 may be a foam comprised of polyols such as polyester or polyether, isocyanate such as toluene diisocyanate, and polymerization modifiers such as amines and tin compounds. In some examples, the manifold layer 210 may be a reticulated polyurethane foam such as used in GRANUFOAM™ Dressing or V.A.C. VERAFLO™ Dressing, both available from KCI of San Antonio, Texas.

In some embodiments, one or both of the first manifold layer 215 and the second manifold layer 220 may be formed by a felting process. Any porous foam suitable for felting may be used, including the example foams mentioned herein, such as GRANUFOAM™ Dressing. Felting comprises a thermoforming process that permanently compresses a foam to increase the density of the foam while maintaining interconnected pathways. Felting may be performed by any known methods, which may include applying heat and pressure to a porous material or foam material. Some methods may include compressing a foam blank between one or more heated platens or dies (not shown) for a specified period of time and at a specified temperature. The direction of compression may be along the thickness of the foam blank.

The period of time of compression may range from 10 minutes up to 24 hours, though the time period may be more or less depending on the specific type of porous material used. Further, in some examples, the temperature may range between 120° C. to 260° C. Generally, the lower the temperature of the platen, the longer a porous material must be held in compression. After the specified time period has elapsed, the pressure and heat will form a felted structure or surface on or through the porous material or a portion of the porous material.

The felting process may alter certain properties of the original material, including pore shape and/or size, elasticity, density, and density distribution. For example, struts that define pores in the foam may be deformed during the felting process, resulting in flattened pore shapes. The deformed struts can also decrease the elasticity of the foam. The density of the foam is generally increased by felting. In some embodiments, contact with hot-press platens in the felting process can also result in a density gradient in which the density is greater at the surface and the pores size is smaller at the surface. In some embodiments, the felted structure may be comparatively smoother than any unfinished or non-felted surface or portion of the porous material. Further, the pores in the felted structure may be smaller than the pores throughout any unfinished or non-felted surface or portion of the porous material. In some examples, the felted structure may be applied to all surfaces or portions of the porous material. Further, in some examples, the felted structure may extend into or through an entire thickness of the porous material such that the all of the porous material is felted.

A felted foam may be characterized by a firmness factor, which is indicative of the compression of the foam. The firmness factor of a felted foam can be specified as the ratio of original thickness to final thickness. A compressed or felted foam may have a firmness factor greater than 1. The degree of compression may affect the physical properties of the felted foam. For example, felted foam has an increased effective density compared to a foam of the same material that is not felted. The felting process can also affect fluid-to-foam interactions. For example, as the density increases, compressibility or collapse may decrease. Therefore, foams which have different compressibility or collapse may have different firmness factors. In some example embodiments, a firmness factor can range from about 2 to about 10, preferably about 3 to about 5. For example, the firmness factor of the manifold layer 210 felted foam may be about 5 in some embodiments. There is a general linear relationship between firmness level, density, pore size (or pores per inch) and compressibility. For example, foam that is felted to a firmness factor of 3 will show a three-fold density increase and compress to about a third of its original thickness.

In some embodiments, one or more suitable foam blanks (e.g. of pre-felted foam) may be used for forming one or both of the first manifold layer 215 and the second manifold layer 220. The foam blank(s) may have about 40 to about 50 pores per inch on average, a density of about 1.3 to about 1.6 lb/ft$^3$, a free volume of about 90% or more, an average pore size in a range of about 400 to about 600 microns, a 25% compression load deflection of at least 0.35 pounds per square inch, and/or a 65% compression load deflection of at least 0.43 pounds per square inch. In some embodiments, the foam blank(s) may have a thickness greater than 10 millimeters, for example 10-35 millimeters, 10-25 millimeters, 10-20 millimeters, or 15-20 millimeters. In some embodiments, the foam blank(s) may be felted to provide denser foam for one or both of the first manifold layer 215 and the second manifold layer 220. For example, one or more foam blanks may be felted to a firmness factor of 2-10 to form one or more of the first manifold layer 215 and the second manifold layer 220. In some embodiments, the foam blank may be felted to a firmness factor of 3-7. Some embodiments may felt the foam blank to a firmness factor of 5.

In some embodiments, the first manifold layer 215 may be an unfelted open-cell foam having a free volume of about 90%, a density in a range of about 1.3 to about 1.60 lb/ft$^3$, about 40 to about 50 pores per inch on average, and/or average pore size of about 400 to about 600 microns. In some embodiments, the second manifold layer 220 may be an open-cell foam having a free volume in a range of about 9% to about 45%, a density in a range of about 2.6 to about 16 lb/ft$^3$, about 80 to about 500 pores per inch on average as measured in the direction of compression, an average pore size in a range of about 40 to about 300 microns as measured in the direction of compression, and/or a 25% compression load deflection of about 0.7 to about 3.5 pounds per square inch and a 65% compression load deflection of about 0.86 to about 4.3 pounds per square inch, which may be particularly advantageous under negative pressure. In some embodiments, the second manifold layer 220 may be an open-cell foam having a free volume in a range of about 18% to about 45%, a density in a range of about 2.6 to about 8 lb/ft$^3$, about 80 to about 250 pores per inch on average (e.g., as measured in the direction of compression), an average pore size in a range of about 80 to about 300 microns (e.g., as measured in the direction of compression), and/or a 25% compression load deflection of about 0.7 to about 1.75 pounds per square inch and a 65% compression load deflection of about 0.86 to about 2.15 pounds per square inch, which may be particularly advantageous under negative pressure. For example, the denser second manifold layer 220 may better resist the compressive effects when used under a compression garment and/or may better maintain fluid flow when under negative pressure.

In some embodiments, the density of the second manifold layer 220 may be about 3.9 to about 4.8 lb/ft$^3$. In some embodiments, the free volume of the second manifold layer 220 may be about 30%. In some embodiments, the average pore size of the second manifold layer 220 may be about 133 to about 200 microns. In some embodiments, the second manifold layer 220 may have about 120 to about 150 pores per inch on average. In some embodiments, the second manifold layer 220 may have a 25% compression load deflection of at least 1.05 pounds per square inch and a 65% compression load deflection of at least 1.29 pounds per square inch. In some embodiments, the density of the second manifold layer 220 may be about 6.5 to about 8.0 lb/ft$^3$. In some embodiments, the free volume of the second manifold layer 220 may be about 18%. In some embodiments, the average pore size of the second manifold layer 220 may be about 80 to about 120 microns. In some embodiments, the second manifold layer 220 may have about 200 to about 250 pores per inch on average. In some embodiments, the second manifold layer 220 may have a 25% compression load deflection of at least 1.75 pounds per square inch and a 65% compression load deflection of at least 2.15 pounds per square inch. In some embodiments the second manifold layer 220 may have a higher density than the density of the first manifold layer 215.

In some embodiments, the first manifold layer 215 may be felted. In some embodiments, the first manifold layer 215 may be an open-cell foam having a free volume in a range of about 9% to about 45%, a density in a range of about 2.6 to about 16 lb/ft$^3$, about 80 to about 500 pores per inch on average as measured in the direction of compression, an average pore size in a range of about 40 to about 300 microns as measured in the direction of compression, and/or a 25% compression load deflection of about 0.7 to about 3.5 pounds per square inch and a 65% compression load deflection of about 0.86 to about 4.3 pounds per square inch, which may be particularly advantageous under negative pressure. In some embodiments, the first manifold layer 215 may be an open-cell foam having a free volume in a range of about 18% to about 45%, a density in a range of about 2.6 to about 8 lb/ft³, about 80 to about 250 pores per inch on average as measured in the direction of compression, an average pore size in a range of about 80 to about 300 microns as measured in the direction of compression, and/or a 25% compression load deflection of about 0.7 to about 1.75 pounds per square inch and a 65% compression load deflection of about 0.86 to about 2.15 pounds per square inch, which may be particularly advantageous under negative pressure. For example, the denser first manifold layer 215 may better resist the compressive effects when used under a compression garment and/or may better maintain fluid flow when under negative pressure.

In some embodiments, the density of the first manifold layer 215 may be about 3.9 to about 4.8 lb/ft³. In some embodiments, the free volume of the first manifold layer 215 may be about 30%. In some embodiments, the average pore size of the first manifold layer 215 may be about 133 to about 200 microns. In some embodiments, the first manifold layer 215 may have about 120 to about 150 pores per inch on average. In some embodiments, the first manifold layer 215 may have a 25% compression load deflection of at least 1.05 pounds per square inch and a 65% compression load deflection of at least 1.29 pounds per square inch. In some embodiments, the density of the first manifold layer 215 may be about 6.5 to about 8.0 lb/ft³. In some embodiments, the free volume of the first manifold layer 215 may be about 18%. In some embodiments, the average pore size of the first manifold layer 215 may be about 80 to about 120 microns. In some embodiments, the first manifold layer 215 may have about 200 to about 250 pores per inch on average. In some embodiments, the first manifold layer 215 may have a 25% compression load deflection of at least 1.75 pounds per square inch and a 65% compression load deflection of at least 2.15 pounds per square inch.

In some embodiments, only the first manifold layer 215 is felted. In some embodiments, only the second manifold layer 220 is felted. In some embodiments, both the first manifold layer 215 and the second manifold layer 220 are felted. In embodiments in which the first manifold layer 215 is felted, the contact layer 205 may be coupled to the first manifold layer 215 during the felting process.

As further shown in FIG. 2A, the second manifold layer 220 may have one or more holes 230, which can be distributed uniformly or randomly across the second manifold layer 220. The plurality of holes 230 extending through the second manifold layer 220 may form walls 235 extending through the second manifold layer 220. The holes 230 may be configured to provide anisotropic contractive properties to the tissue interface 120 in response to the application of negative pressure to the tissue interface 120.

Figure 2B:
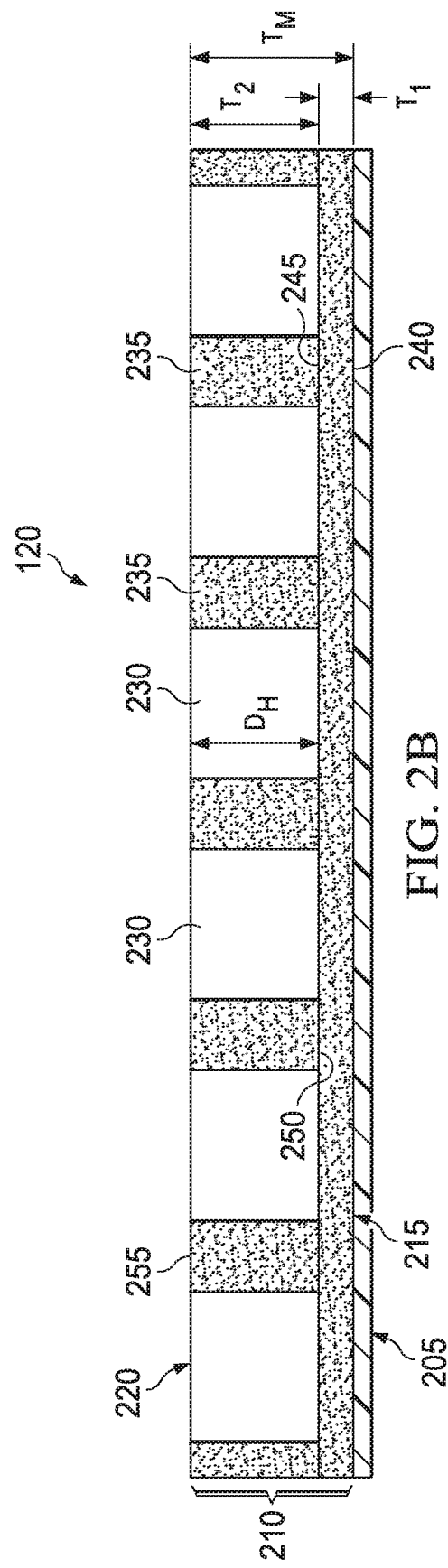
FIG. 2B is a cross-sectional view of the assembled example tissue interface of FIG. 2A along line 2B-2B.

FIG. 2B is a cross-sectional view of the assembled tissue interface 120 of FIG. 2A along line 2B-2B. As shown in FIG. 2B, the first manifold layer 215 may include a first side 240 configured to face a tissue site, a second side 245 opposite the first side 240, and a thickness $T_1$ between the first side 240 and the second side 245. The second manifold layer 220 may include a first side 250 configured to face a tissue site, a second side 255 opposite the first side 250, and a thickness $T_2$ between the first side 250 and the second side 255. The first side 250 of the second manifold layer 220 may be coupled to the second side 245 of the first manifold layer 215. If coupled together, the first manifold layer 215 and the second manifold layer 220 may form the manifold layer 210. In some embodiments, the first side 240 of the first manifold layer 215 may be on a first side of the manifold layer 210 and the second side 255 of the second manifold layer 220 may be on a second side of the manifold layer 210. In some embodiments, the manifold layer 210 may have a thickness $T_M$ equal to the sum of the thickness $T_1$ of the first manifold layer 215 and the thickness $T_2$ of the second manifold layer 220. In some embodiments, for example, the thickness $T_1$ of the first manifold layer 215 may be in a range of about 0.5 millimeters to about 5 millimeters. In some embodiments, the thickness $T_1$ of the first manifold layer 215 may be in a range of about 1 millimeter to about 3 millimeters. In some embodiments, the thickness $T_1$ of the first manifold layer 215 may be about 2 millimeters. In some embodiments, for example, the thickness $T_2$ of the second manifold layer 220 may be in a range of about 3 millimeters to about 9 millimeters. In some embodiments, for example, the thickness $T_2$ of the second manifold layer 220 may be in a range of about 3 millimeters to about 6 millimeters. In some embodiments, the thickness $T_2$ of the second manifold layer 220 may be about 6 millimeters. In some embodiments, the thickness $T_M$ of the manifold layer 210 may be in a range of about 3 millimeters to about 14 millimeters. In some embodiments, the thickness $T_M$ of the manifold layer 210 may be in a range of about 3 millimeters to about 9 millimeters. In some embodiments, the thickness $T_M$ of the manifold layer 210 may be about 8 millimeters.

With continued reference to FIG. 2B, the plurality of holes 230 may extend into the second manifold layer 220 on the second side 255 and may have a hole depth $D_H$ measured from the second side 255. In some embodiments, the hold depth $D_H$ may be equal to the thickness $T_2$ of the second manifold layer 220. In some embodiments, the walls 235 may be parallel to the thickness $T_2$ of the second manifold layer 220. In other embodiments, the walls 235 may be generally perpendicular to the first side 250 and the second side 255 of the second manifold layer 220.

Figures 3A, 3B:
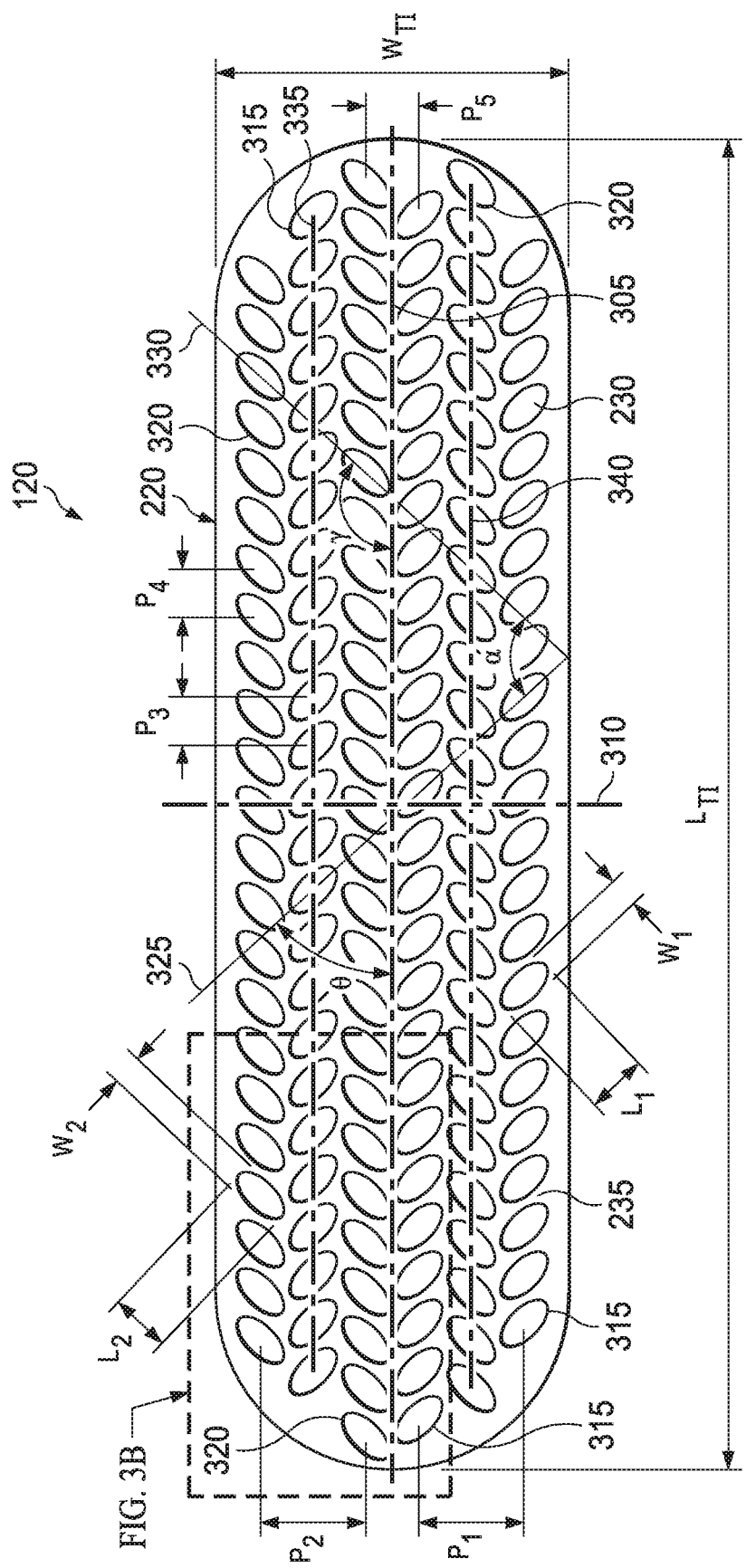
FIG. 3A is a top view of the tissue interface of FIG. 2A.
FIG. 3B is a detail view of the tissue interface of FIG. 3A taken at reference FIG. 3B in FIG. 3A.
Figure 3B:
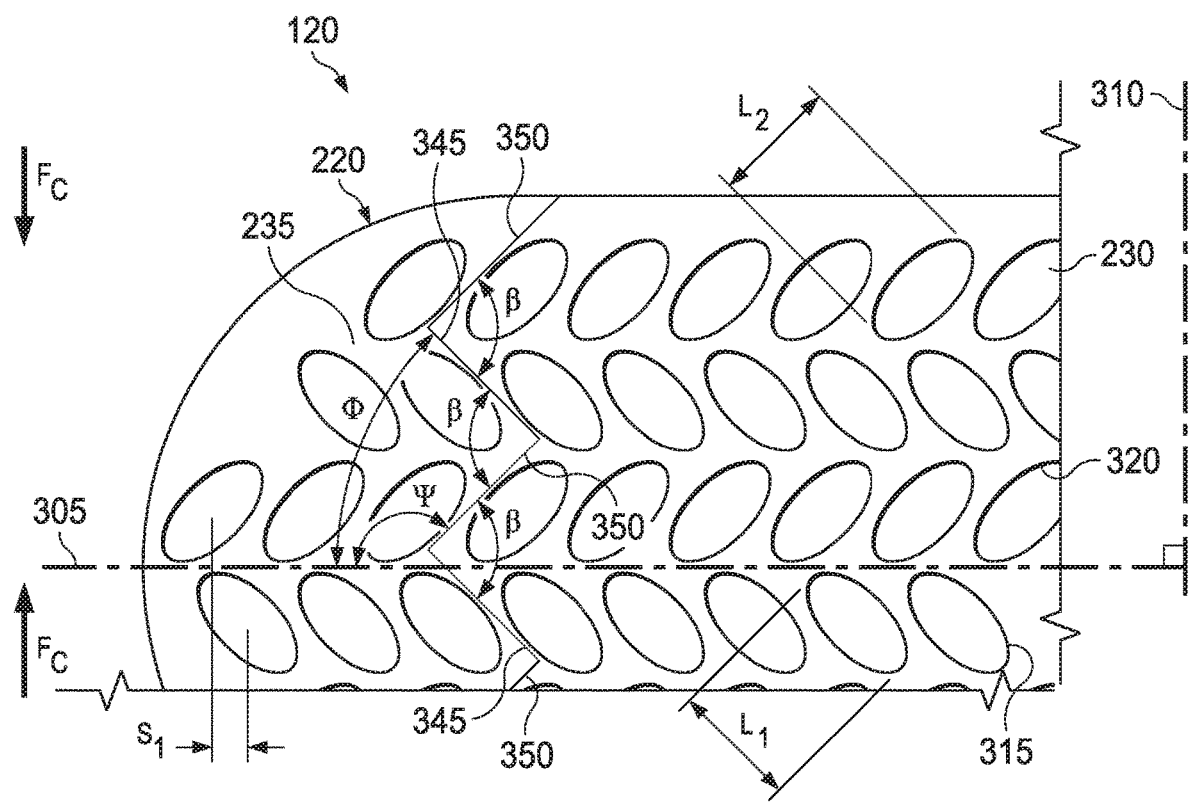

FIG. 3A is a top view of the tissue interface 120 of FIG. 2A. As shown in FIG. 3A, in some embodiments, the tissue interface 120 may have a first orientation line 305 and a second orientation line 310 that is perpendicular to the first orientation line 305. In some embodiments, the first orientation line 305 may be parallel to the length $L_{TI}$ of the tissue interface 120 and the second orientation line 310 may be parallel to the width $W_{TI}$ of the tissue interface 120. Generally, the first orientation line 305 and the second orientation line 310 aid in the description of the tissue interface 120. In some embodiments, the tissue interface 120 may be configured to contract under the application of negative pressure more in a first direction than in a second direction. The first orientation line 305 and the second orientation line 310 may be used to refer to a desired direction of contraction of the tissue interface 120. For example, the desired direction of contraction may be parallel to the second orientation line 310 and perpendicular to the first orientation line 305. In some embodiments, the second orientation line 310 may be a primary contraction axis. In other embodiments, the desired direction of contraction may be parallel to the first orientation line 305 and perpendicular to the second orientation line 310. In still other embodiments, the desired direction of contraction may be at a non-perpendicular angle to both the first orientation line 305 and the second orientation line 310.

As further shown in FIG. 3A, the tissue interface 120 may have a length $L_{TI}$ and a width $W_{TI}$. In some embodiments, if the tissue interface 120 is not subjected to negative pressure, the length $L_{TI}$ may be a nominal or relaxed length, and the width $W_{TI}$ may be a nominal or relaxed width. In some embodiments, the length $L_{TI}$ may be greater than the width $W_{TI}$, such that the width $W_{TI}$ may be less than the length $L_{TI}$. For example, the tissue interface 120 may have an elongate shape. In some embodiments, for example, the tissue interface 120 may have a length $L_{TI}$ to width $W_{TI}$ ratio of at least 4:1. In some embodiments, the length $L_{TI}$ may be equal to the width $W_{TI}$. In some embodiments, the length $L_{TI}$ may be less than the width $W_{TI}$. In some embodiments, one or more of the contact layer 205, the first manifold layer 215, and the second manifold layer 220 may be coextensive or congruent with one another. For example, the contact layer 205, the first manifold layer 215, and the second manifold layer 220 may have the same length and width. In some embodiments, the contact layer 205, the first manifold layer 215, and the second manifold layer 220 may have the same size and shape. In some embodiments, the length and width of the contact layer 205, the first manifold layer 215, and the second manifold layer 220 may be equal to the length $L_{TI}$ and a width $W_{TI}$ of the tissue interface 120. In some embodiments, the length and width of the manifold layer 210 may be equal to the length $L_{TI}$ and a width $W_{TI}$ of the tissue interface 120. In some embodiments, each of the contact layer 205, the first manifold layer 215, and the second manifold layer 220 may have an elongate length. In some embodiments, each of the contact layer 205, the first manifold layer 215, and the second manifold layer 220 may have a length and a width, wherein the length is greater than the width.

Although the tissue interface 120 is shown as having an elongate stadium shape, the tissue interface 120 may have other shapes. For example, the tissue interface 120 may have a rectangular, diamond, square, or circular shape. In some embodiments, the shape of the tissue interface 120 may be selected to accommodate the type of tissue site being treated. For example, the tissue interface 120 may have an oval or circular shape to accommodate an oval or circular tissue site. In some embodiments, each of the contact layer 205, the first manifold layer 215, and the second manifold layer 220 may have an elongate stadium shape.

As further illustrated in FIG. 3A, the holes 230 may include a first plurality of holes 315 and a second plurality of holes 320. Each of the first plurality of holes 315 and the second plurality of holes 320 may be ovoid shaped. In some embodiments where the holes 230 are ovoid shaped, each of the first plurality of holes 315 may have a length $L_1$ and a width $W_1$ perpendicular to the length $L_1$, and each of the second plurality of holes 320 may have a length $L_2$ and a width $W_2$ perpendicular to the length $L_2$. In some embodiments, the length $L_1$ may be equal to the length $L_2$. In some embodiments, the width $W_1$ may be equal to the width $W_2$. In the example of FIG. 3A, $L_1$ and $L_2$ may be substantially equal, and $W_1$ and $W_2$ may be substantially equal, within acceptable manufacturing tolerances. In some embodiments, $L_1$ and $L_2$ may be about 10 millimeters, and $W_1$ and $W_2$ may be about 5 millimeters.

The first plurality of holes 315 and the second plurality of holes 320 may be distributed across the second manifold layer 220 in one or more rows in one direction or in different directions. In some embodiments, the rows of the first plurality of holes 315 and the second plurality of holes 320 may be offset or staggered. In some embodiments, the length $L_1$ of the first plurality of holes 315 and the length $L_2$ of the second plurality of holes 320 may be positioned at an angle relative to the length $L_{TI}$ of the tissue interface 120. In some embodiments, the length $L_1$ of one or more of the first plurality of holes 315 in a first row may point toward the width $W_2$ of one or more of the second plurality of holes 320 in a second row. In some embodiments, the length $L_2$ of one or more of the second plurality of holes 320 in a second row may point toward the width $W_1$ of one or more of the first plurality of holes 315 in a first row. The pattern of FIG. 3A may be characterized as a herringbone pattern.

In example embodiments, each of the first plurality of holes 315 may have a first long axis. The first long axis may be parallel to the length $L_1$ of the first plurality of holes 315. In some embodiments, the first long axis may be parallel to a first reference line 325 running in a first direction. In illustrative examples, each of the second plurality of holes 320 may have a second long axis. The second long axis may be parallel to the length $L_2$ of the second plurality of holes 320. In example embodiments, the second long axis may be parallel to a second reference line 330 running in a second direction. In some embodiments, one or both of the first reference line 325 and the second reference line 330 may be defined relative to the first orientation line 305 of the second manifold layer 220. For example, one or both of the first reference line 325 and the second reference line 330 may be parallel or coincident with the first orientation line 305 of the second manifold layer 220. In some illustrative embodiments, one or both of the first reference line 325 and the second reference line 330 may be rotated an angle relative to the first orientation line 305 of the second manifold layer 220. For example, the first reference line 325 may form an angle θ with the first orientation line 305 and the second reference line 330 may form an angle γ with the first orientation line 305. In example embodiments, an angle α may define the angle between the first reference line 325 and the second reference line 330. In some embodiments, the angle θ may be less than about 90°. In some embodiments, the angle θ may be in a range from about 30° to about 70°. In some embodiments, the angle θ may be about 45°. In some embodiments, the angle γ may be greater than about 90°. In some embodiments, the angle γ may be in a range from about 110° to about 150°. In some embodiments, the angle γ may be about 135°. In some embodiments, the angle α may be in a range from about 40° to about 120°. In some embodiments, the angle α may be about 90°.

In some embodiments, as the angle θ between first reference line 325 and the first orientation line 305 decreases and the angle γ between the second reference line 330 and the first orientation line 305 increases, such that the first reference line 325 and the second reference line 330 approach becoming parallel to the first orientation line 305, the compressibility of the tissue interface 120 parallel to the second orientation line 310 may increase. Consequently, if negative pressure is applied to the tissue interface 120, the tissue interface 120 may contract more in a direction parallel to the second orientation line 310 than in a direction parallel to the first orientation line 305. By increasing the compressibility of the tissue interface 120 in a direction parallel to the second orientation line 310, the tissue interface 120 may collapse to apply a closing force $F_C$ to a tissue site, as described in more detail below.

In some example embodiments, the centroid of each of the first plurality of holes 315 within a row may intersect a third reference line 335 running in a third direction. In illustrative embodiments, the centroid of each of the second plurality of holes 320 within a row may intersect a fourth reference line 340 running in a fourth direction. In the example of FIG. 3A, the third reference line 335 and the fourth reference line 340 may be parallel to the first orientation line 305.

The pattern of holes 230 may also be characterized by a pitch, which indicates the spacing between corresponding points on holes 230 within a pattern. In example embodiments, pitch may indicate the spacing between the centroids of holes 230 within the pattern. Some patterns may be characterized by a single pitch value, while others may be characterized by at least two pitch values. For example, if the spacing between centroids of the holes 230 is the same in all orientations, the pitch may be characterized by a single value indicating the spacing between centroids in adjacent rows. In some embodiments, a pattern comprising a first plurality of holes 315 and a second plurality of holes 320 may be characterized by five pitch values, $P_1$, $P_2$, $P_3$, $P_4$, and $P_5$. $P_1$ may be the spacing between the centroids of each of the first plurality of holes 315 in adjacent rows perpendicular to the third reference line 335. $P_2$ may be the spacing between the centroids of each of the second plurality of holes 320 in adjacent rows perpendicular to the fourth reference line 340. $P_3$ may be the spacing between adjacent centroids of each of the first plurality of holes 315 within each row parallel to the third reference line 335. $P_4$ may be the spacing between adjacent centroids of each of the second plurality of holes 320 within each row parallel to the to the fourth reference line 340. $P_5$ may be the spacing between the centroids of each of the first plurality of holes 315 and each of the second plurality of holes 320 in adjacent rows. In the example of FIG. 3A, $P_1$ and $P_2$ may be substantially equal, and $P_3$ and $P_4$ may be substantially equal, within acceptable manufacturing tolerances. In some embodiments where $P_1$ equals $P_2$ ($P_1=P_2$), then $P_5$ may be equal to half of $P_1$ and $P_2$ ($P_5=0.5\times P_1=0.5\times P_2$). In some embodiments, $P_1$ and $P_2$ may be about 17.5 millimeters, $P_3$ and $P_4$ may be about 8 millimeters, and P5 may be about 8.75 millimeters.

The plurality of holes 230 may form a percent open area the tissue interface 120. The percent open area of the plurality of holes 230 may be equal to the percentage of the area of the plurality of holes 230 to the total surface area of the first side of the second manifold layer 220 of the tissue interface 120. In some embodiments, the percent open area may be between about 40% and about 60%. In other embodiments, the percent open area may be about 56%.

FIG. 3B is a detail view of the tissue interface 120 taken at reference FIG. 3B in FIG. 3A. In some patterns, the rows may be offset or staggered. The stagger may be characterized by an orientation of corresponding points in successive rows relative to an edge or other reference line associated with the second manifold layer 220. In some embodiments, the rows of the first plurality of holes 315 may be staggered with the rows of the second plurality of holes 320. In some embodiments, the stagger may be characterized by a stagger value $S_1$, where $S_1$ may be the spacing between centroids of each of the first plurality of holes 315 and the second plurality of holes 320 in adjacent rows parallel to the to the fourth reference line 340. In some embodiments, $S_1$ may be about 2 to about 10 millimeters. In some embodiments, $S_1$ may be about 3 millimeters.

In some embodiments, the plurality of walls 235 can be considered to have a concertinaed shape. The concertinaed shape may be formed by a plurality of alternating first wall portions 345 and second wall portions 350. The first wall portions 345 may be oriented at an angle Φ with respect to the first orientation line 305. In some embodiments, the angle Φ of the first wall portions 345 may be equal to the angle θ. In the example of FIG. 3B, the first wall portions 345 may be about 45° with respect to the first orientation line 305. The second wall portions 350 may be oriented at an angle Ψ with respect to the first orientation line 305. In some embodiments, the angle Ψ of the second wall portions 350 may be equal to the angle γ. In the example of FIG. 3B, the second wall portions 350 may be about 135° with respect to the first orientation line 305. In some embodiments, the first wall portions 345 may be parallel to the length $L_1$ of the first plurality of holes 315, and the second wall portions 350 may be parallel to the length $L_2$ of the second plurality of holes 320. The first wall portions 345 and second wall portions 350 may have an angle β between each wall portion. In some embodiments, β may be equal to 180° minus α (β=180°−α). In some embodiments, β may be about 90°. In some embodiments, as the angle β between each wall portion decreases, the compressibility of the tissue interface 120 parallel to the second orientation line 310 may increase. Consequently, if negative pressure is applied to the tissue interface 120, the tissue interface 120 may contract more in a direction parallel to the second orientation line 310 than in a direction parallel to the first orientation line 305. By increasing the compressibility of the tissue interface 120 in a direction parallel to the second orientation line 310, the tissue interface 120 may collapse to apply a closing force $F_C$ to a tissue site, as described in more detail below.

Figure 4:
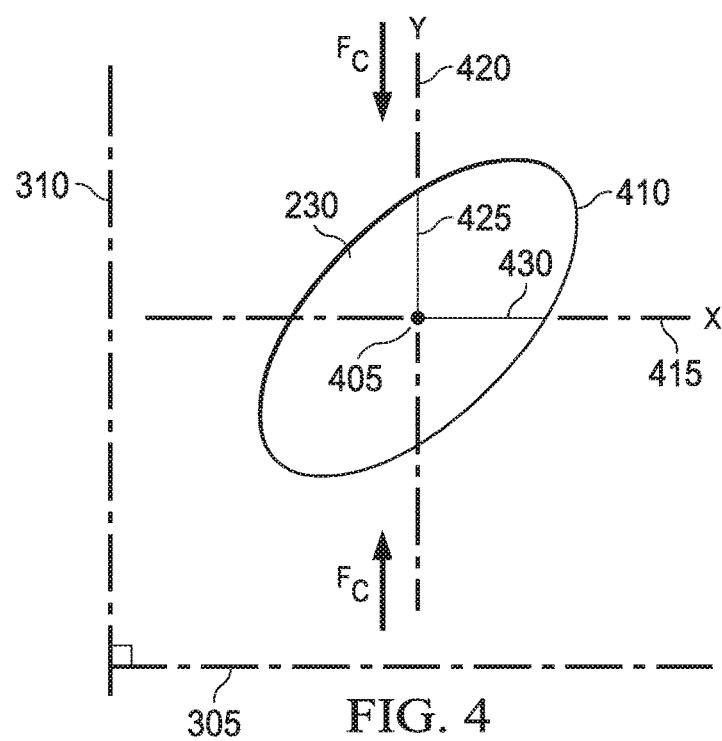
FIG. 4 is a top view of an example of a hole having an ovoid shape that may be associated with the tissue interface of FIG. 3A.

FIG. 4 is a top view of an example of a single hole 230 having an ovoid shape that may be associated with the tissue interface of FIG. 3A. The hole 230 may include a centroid 405 and a perimeter 410. The hole 230 may have a perforation shape factor (PSF). The perforation shape factor (PSF) may represent an orientation of the hole 230 relative to the first orientation line 305 and the second orientation line 310. Generally, the perforation shape factor (PSF) is a ratio of ½ a maximum length of the hole 230 that is parallel to the desired direction of contraction to ½ a maximum length of the hole 230 that is perpendicular to the desired direction of contraction. For descriptive purposes, the desired direction of contraction is parallel to the second orientation line 310. The desired direction of contraction may be indicated by the closing force $F_C$. For reference, the hole 230 may have an X-axis 415 extending through the centroid 405 parallel to the first orientation line 305, and a Y-axis 420 extending through the centroid 405 parallel to the second orientation line 310. In some embodiments, the perforation shape factor (PSF) of the hole 230 may be defined as a ratio of a line segment 425 on the Y-axis 420 extending from the centroid 405 to the perimeter 410 of the hole 230, to a line segment 430 on the X-axis 415 extending from the centroid 405 to the perimeter 410 of the hole 230. For example, if a length of the line segment 425 is 2.5 mm and the length of the line segment 430 is 2.5 mm, the perforation shape factor (PSF) would be 2.5/2.5 or about 1. In some embodiments, the holes 230 may have an ovoid shape as shown. In other embodiments, the holes 230 may have a circular, oval, triangular, square, hexagonal, irregular, or amorphous shape.

In some embodiments, the holes 230 may be formed during molding of the second manifold layer 220. In other embodiments, the holes 230 may be formed by cutting, melting, or vaporizing the second manifold layer 220 after the second manifold layer 220 is formed. For example, the holes 230 may be formed in the second manifold layer 220 by laser cutting the felted foam of the second manifold layer 220. In some embodiments, the holes 230 may have an effective diameter, wherein the effective diameter of a non-circular area is defined as a diameter of a circular area having the same surface area as the non-circular area. In some embodiments, each hole 230 may have an effective diameter of about 3.5 millimeters. In other embodiments, each hole 230 may have an effective diameter in a range of about 5 millimeters to about 20 millimeters. The effective diameter of the holes 230 should be distinguished from the porosity of the material forming the walls 235 of the second manifold layer 220. Generally, an effective diameter of the holes 230 is an order of magnitude larger than the effective diameter of the pores of a material forming the second manifold layer 220. For example, the effective diameter of the holes 230 may be larger than about 1 millimeters, while the walls 235 may be formed from GRANUFOAM™ Dressing material having a pore size less than about 600 microns. In some embodiments, the pores of the walls 235 may not create openings that extend all the way through the material.

Figure 5A:
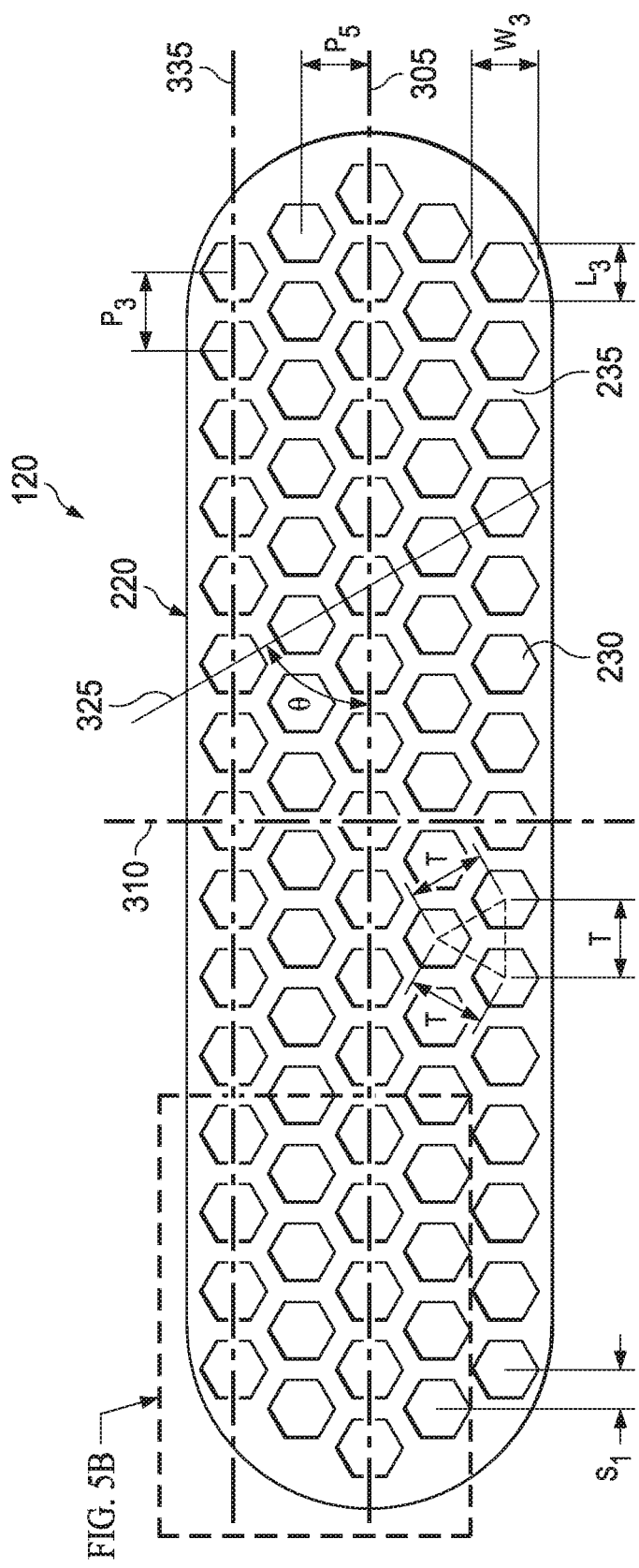
FIG. 5A is a top view of another example of a tissue interface that can be associated with some embodiments of the therapy system of FIG. 1.

FIG. 5A is a top view of another example of the tissue interface 120, illustrating additional details that may be associated with some embodiments of the therapy system 100. As shown in FIG. 5A, the plurality of holes 230 may be hexagonal shaped. In some embodiments where the holes are hexagonal shaped, each of the holes 230 may have a length $L_3$ and a width $W_3$. In some embodiments, $L_3$ may be about 5 millimeters, and $W_3$ may be about 6 millimeters. The plurality of holes 230 may be distributed across the second manifold layer 220 in one or more rows in one direction or in different directions. The pattern of FIG. 5A may be characterized as a hexagonal pattern. The pattern of the plurality of holes 230 may be described with reference to the angle θ between the first orientation line 305 and the first reference line 325, the third reference line 335, the pitch $P_3$, the pitch $P_5$, and the stagger S1. In the example of FIG. 5A, the angle θ may be about 60°, the third reference line 335 may be parallel to the first orientation line 305, $P_3$ may be about 7 millimeters, $P_5$ may be about 5.5 millimeters, and $S_1$ may be about 3.5 millimeters. In some embodiments, the pattern of holes 230 in FIG. 5 may be characterized as a staggered pattern of hexagonal holes having a triangular pitch T, where T may be in a range from about 5 millimeters to about 20 millimeters. In some embodiments, the T may be about 15 millimeters. In some embodiments, wherein the plurality of holes 230 have a hexagonal shape, the percent open area may be between about 40% and about 60%. In other embodiments, the percent open area may be about 55%.

Figure 5B:
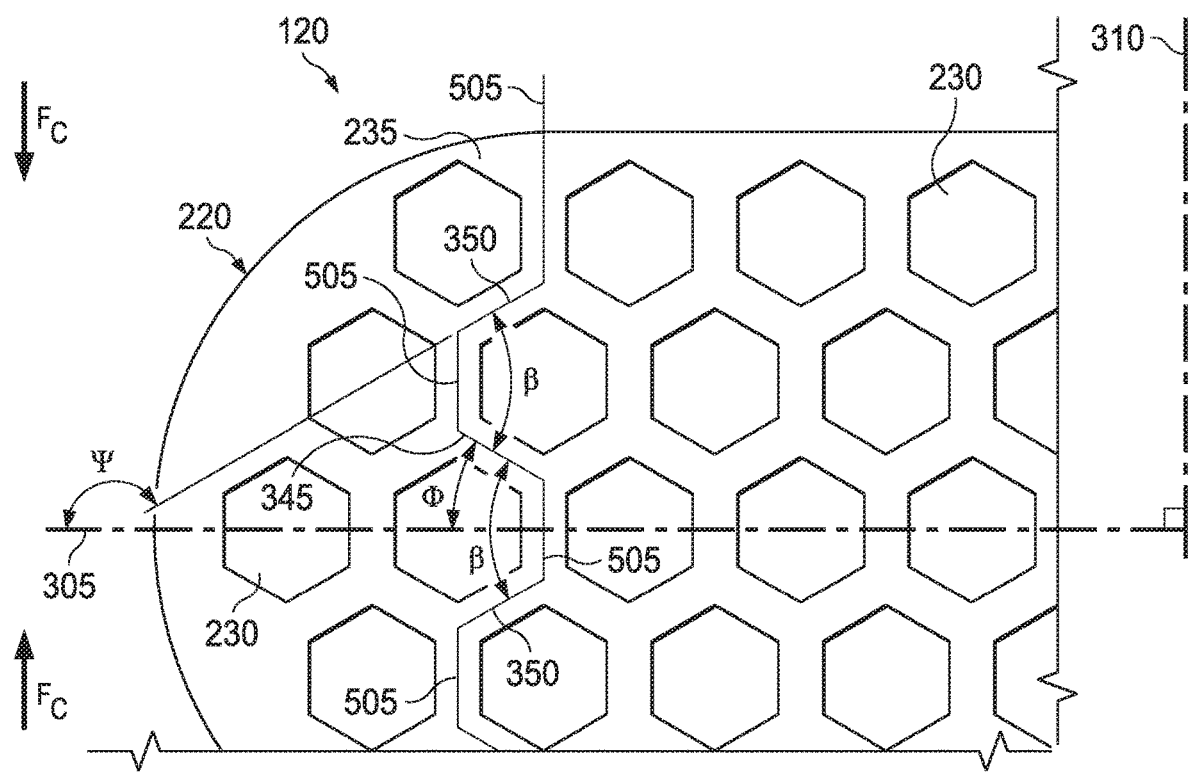
FIG. 5B is a detail view of the tissue interface of FIG. 5A taken at reference FIG. 5B in FIG. 5A.

FIG. 5B is a detail view of the tissue interface 120 taken at reference FIG. 5B in FIG. 5A. As shown in FIG. 5B, the plurality of hexagonal holes 230 may cooperate to form the plurality of walls 235 that can be considered to have a concertinaed shape. The concertinaed shape may be formed by a plurality of alternating first wall portions 345 and second wall portions 350, with a third wall portion 505 in between each first wall portion 345 and second wall portion 350. In some embodiments, Φ may be about 30°, Ψ may be about 150°, and β may be about 60°. As shown in the example of FIG. 5B, the third wall portion 505 may be perpendicular to the first orientation line 305.

Figure 6:
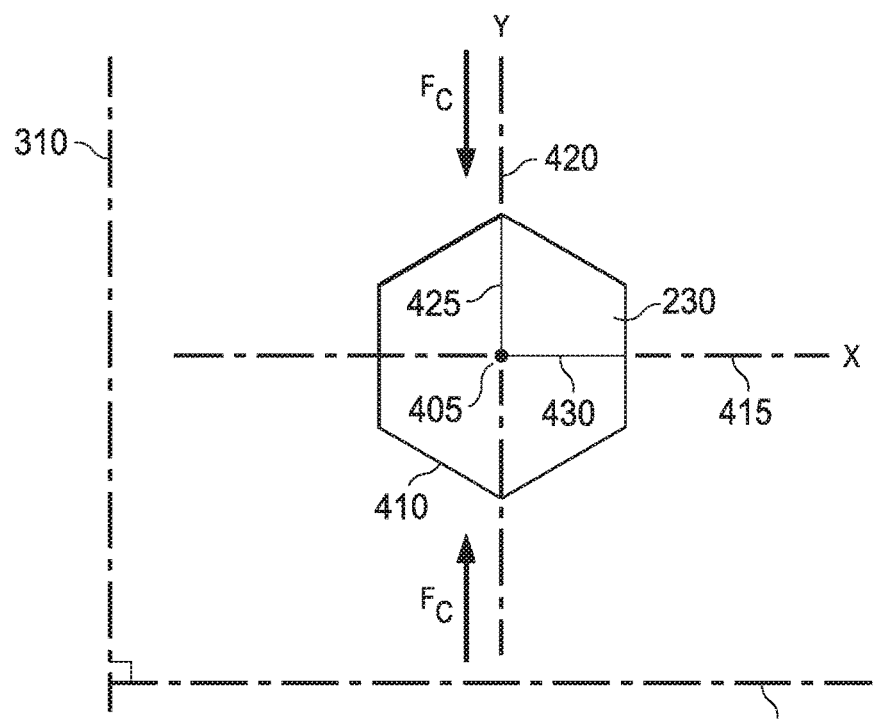
FIG. 6 is a top view of an example of a hole having a hexagonal shape that may be associated with the tissue interface of FIG. 5A.

FIG. 6 is a top view of an example of a single hole 230 having a hexagonal shape that may be associated with the tissue interface of FIG. 5A. For reference, the hole 230 may have an X-axis 415 extending through the centroid 405 between opposing sides of the hexagon and parallel to the first orientation line 305, and a Y-axis 420 extending through the centroid 405 between opposing vertices of the hexagon and parallel to the second orientation line 310. If a length of the line segment 425 on the Y-axis 420 is 2.69 mm and the length of the line segment 430 on the X-axis is 2.5 mm, the perforation shape factor (PSF) would be 2.69/2.5 or about 1.08. In other embodiments, the hole 230 may be oriented relative to the first orientation line 305 and the second orientation line 310 so that the perforation shape factor (PSF) may be about 1.07 or 1.1.

FIG. 7A is a top view of another example of the tissue interface 120, illustrating additional details that may be associated with some embodiments of the therapy system 100. As shown in FIG. 7A, the plurality of holes 230 may be circular shaped. In some embodiments where the holes are circular shaped, each of the holes 230 may have a diameter $D_1$. In some embodiments, $D_1$ may be about 5 millimeters. The plurality of holes 230 may be distributed across the second manifold layer 220 in one or more rows in one direction or in different directions. The pattern of FIG. 7A may be characterized as a staggered circular pattern. The pattern of the plurality of holes 230 may be described with reference to the angle θ between the first orientation line 305 and the first reference line 325, the third reference line 335, the pitch $P_3$, the pitch $P_5$, and the stagger $S_1$. In the example of FIG. 7A, the angle θ may be about 37°, the third reference line 335 may be parallel to the first orientation line 305, $P_3$ may be about 10 millimeters, $P_5$ may be about 3.75 millimeters, and $S_1$ may be about 5 millimeters. In some embodiments, wherein the plurality of holes 230 have a circular shape, the percent open area may be between about 40% and about 60%. In other embodiments, the percent open area may be about 54%.

Figure 7B:
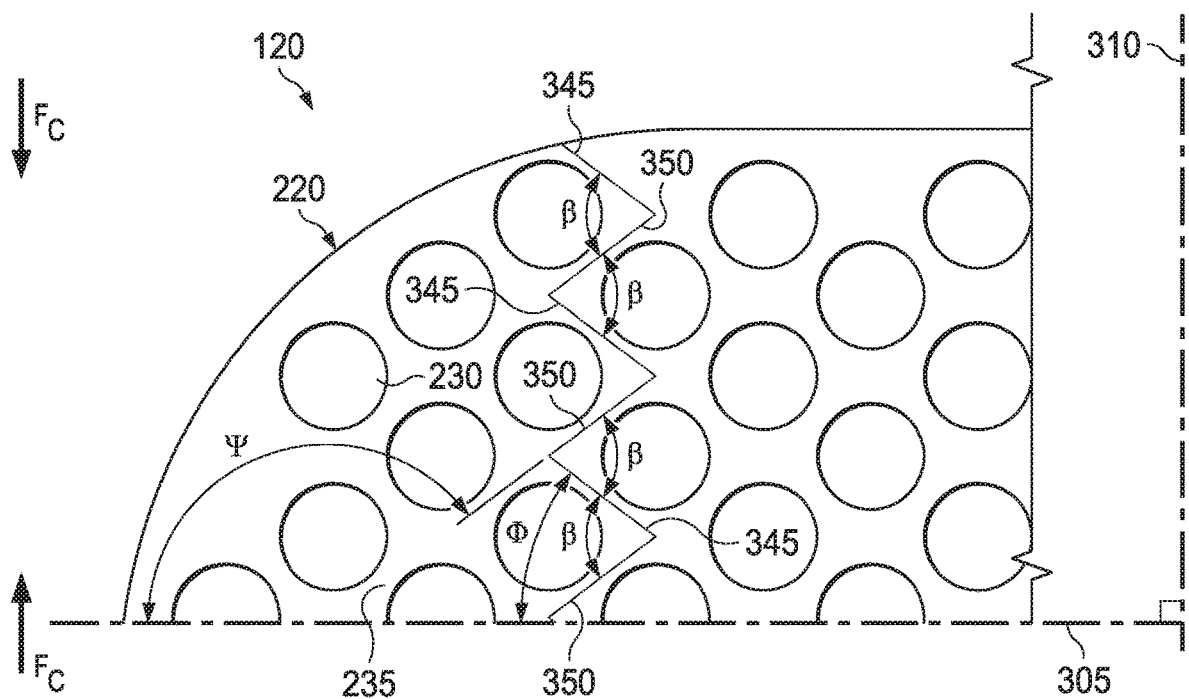
FIG. 7B is a detail view of the tissue interface of FIG. 7A taken at reference FIG. 7B in FIG. 7A.

FIG. 7B is a detail view of the tissue interface 120 taken at reference FIG. 7B in FIG. 7A. As shown in FIG. 7B, the plurality of circular holes 230 may cooperate to form the plurality of walls 235 that can be considered to have a concertinaed shape. The concertinaed shape may be formed by a plurality of alternating first wall portions 345 and second wall portions 350. In some embodiments, Φ may be about 37°, Ψ may be about 143°, and β may be about 74°.

Figure 8:
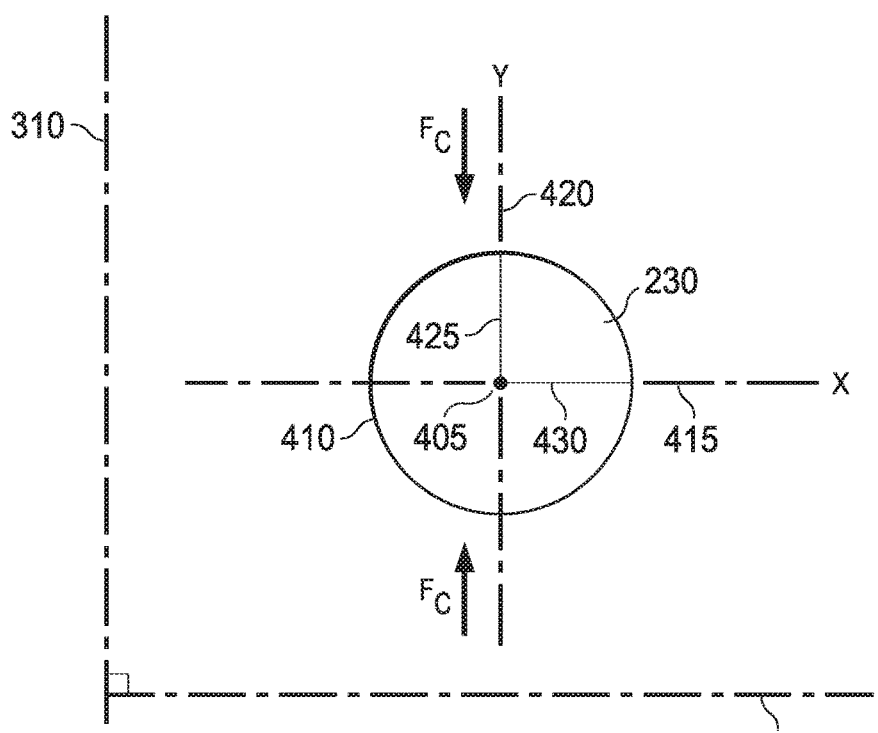
FIG. 8 is a top view of an example of a hole having a circular shape that may be associated with the tissue interface of FIG. 7A.

FIG. 8 is a top view of an example of a single hole 230 having a circular shape that may be associated with the tissue interface of FIG. 7A. For reference, the hole 230 may have an X-axis 415 extending through the centroid 405 parallel to the first orientation line 305, and a Y-axis 420 extending through the centroid 405 parallel to the second orientation line 310. If a length of the line segment 425 on the Y-axis 420 is 2.5 mm and the length of the line segment 430 on the X-axis is 2.5 mm, the perforation shape factor (PSF) would be 2.5/2.5 or about 1.

Figure 9A:
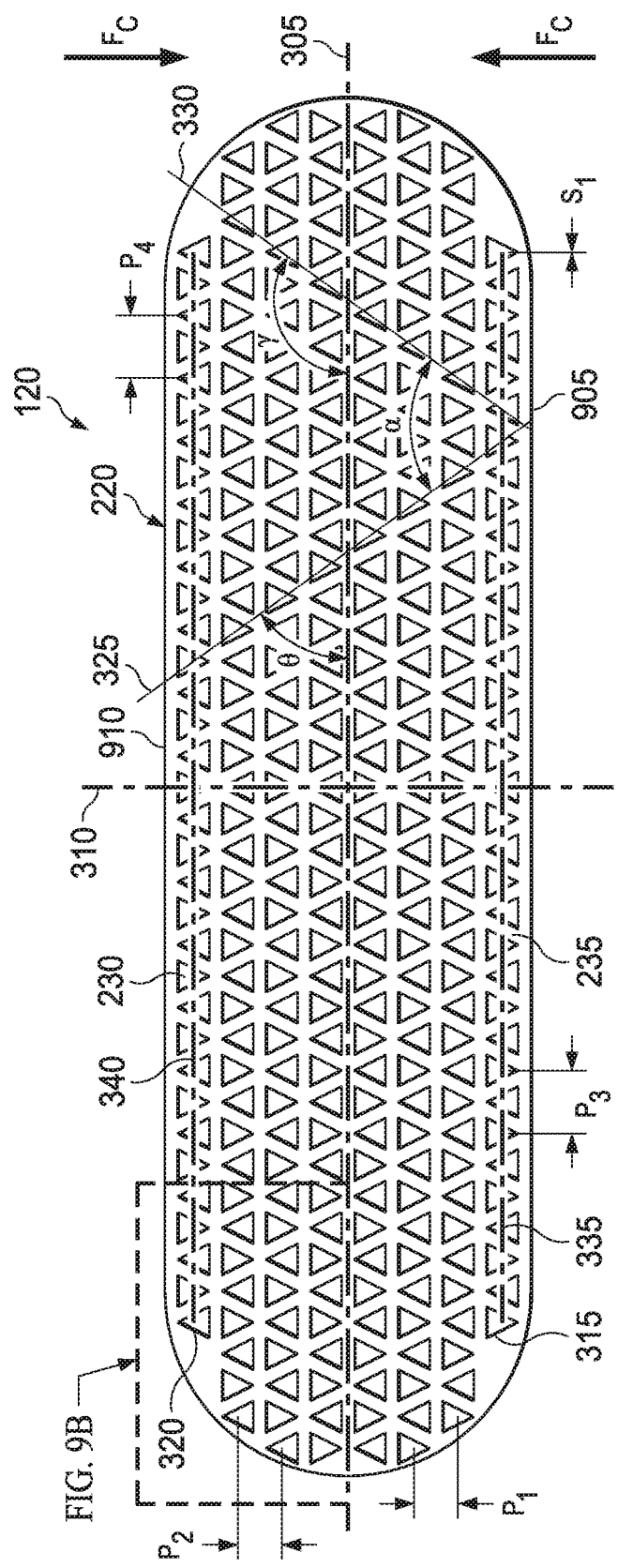
FIG. 9A is a top view of another example of a tissue interface that can be associated with some embodiments of the therapy system of FIG. 1.

FIG. 9A is a top view of an example of the tissue interface 120, illustrating additional details that may be associated with some embodiments of the therapy system 100. As shown in FIG. 9A, the holes 230 may include a first plurality of holes 315 and a second plurality of holes 320. Each of the first plurality of holes 315 and the second plurality of holes 320 may be triangular shaped. The first plurality of holes 315 and the second plurality of holes 320 may be distributed across the second manifold layer 220 in one or more rows in one direction or in different directions. Each of the first plurality of holes 315 may have a first base oriented parallel to the first orientation line 305 and each of the second plurality of holes 320 may have a second base oriented parallel to the first orientation line 305. Each of the first plurality of holes 315 may have a first apex opposite the first base and each of the second plurality of holes 320 may have a second apex opposite the second base, wherein each first apex points opposite each second apex. In some embodiments, the second manifold layer 220 may have a first edge 905 and a second edge 910 opposite the first edge 905, wherein each first apex points toward the first edge 905 and each second apex points toward the second edge 910.

As shown in FIG. 9A, each row of holes 230 may alternate between a hole of the first plurality of holes 315 and a hole of the second plurality of holes 320. In some embodiments, the rows of holes 230 may be mirrored. For example, a second base of a hole of the second plurality of holes 320 may be proximate a first base of a hole of the first plurality of holes 315 in an adjacent row. Additionally, a first apex of a hole of the first plurality of holes 315 may be adjacent to a second apex of a hole of the second plurality of holes 320 in an adjacent row.

The pattern of the first plurality of holes 315 and the second plurality of holes 320 may be described with reference to the angle θ between the first orientation line 305 and the first reference line 325, the angle γ between the first orientation line 305 and the second reference line 330, third reference line 335, fourth reference line 340, pitch values, $P_1$, $P_2$, $P_3$, and $P_4$, and the stagger $S_1$. In some embodiments, the angle θ may be in a range from about 50° to about 70°, the angle γ may be about 110° to about 130°, the third reference line 335 may be parallel to the first orientation line 305, the fourth reference line 340 may be parallel to the first orientation line 305, $P_1$ may be in a range from about 5 to about 20 millimeters, $P_2$ may be about in a range from about 5 to about 20 millimeters, $P_3$ may be in a range from about 10 to about 40 millimeters, $P_4$ may be in a range from about 5 to about 20 millimeters, and $S_1$ may be in a range from about zero to about 10 millimeters. In some embodiments, wherein the plurality of holes 230 have a triangular shape, the percent open area may be between about 40% and about 60%. In other embodiments, the percent open area may be about 40%.

Figure 9B:
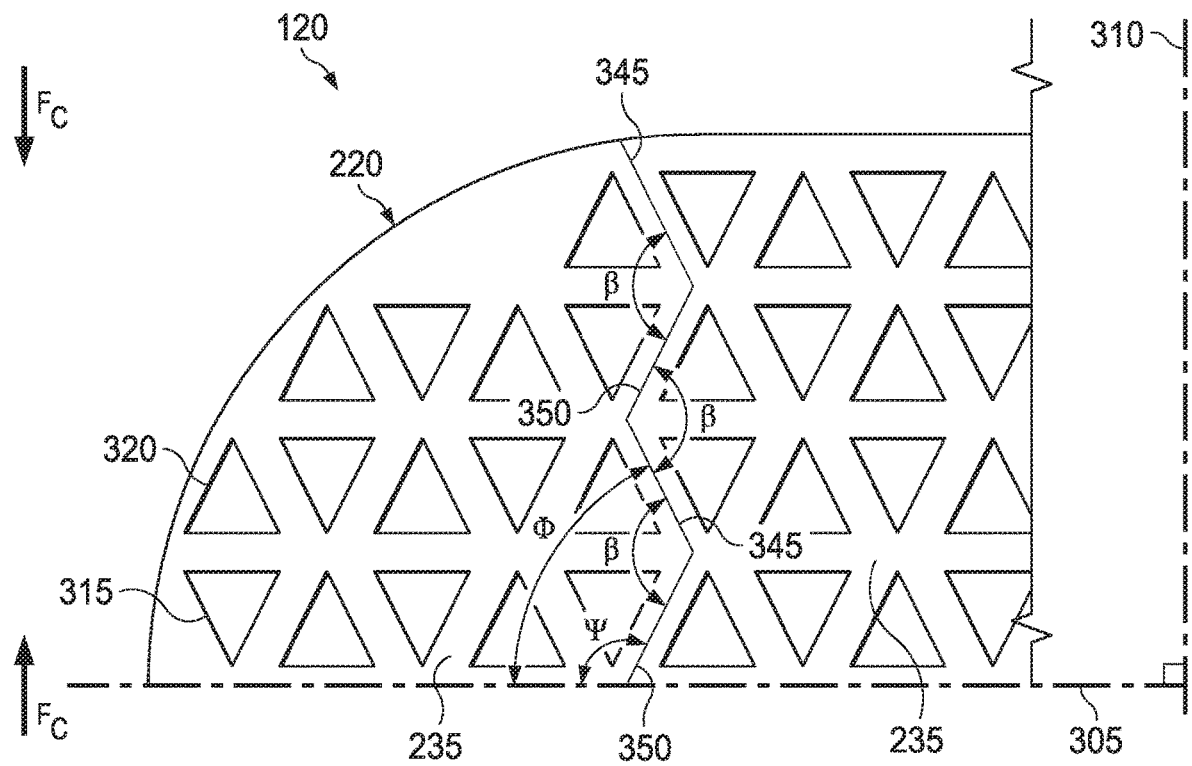
FIG. 9B is a detail view of the tissue interface of FIG. 9A taken at reference FIG. 9B in FIG. 9A.

FIG. 9B is a detail view of the tissue interface 120 taken at reference FIG. 9B in FIG. 9A. As shown in FIG. 9B, the plurality of triangular holes 230 may cooperate to form the plurality of walls 235 that can be considered to have a concertinaed shape. The concertinaed shape may be formed by a plurality of alternating first wall portions 345 and second wall portions 350. In some embodiments, Φ may be about 63°, Ψ may be about 117°, and β may be about 126°.

Figure 10:
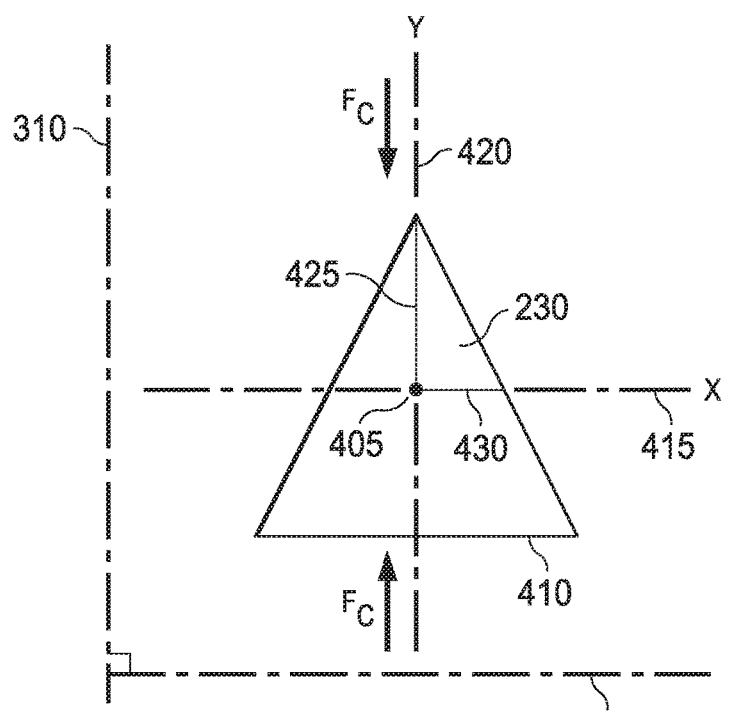
FIG. 10 is a top view of an example of a hole having a triangular shape that may be associated with the tissue interface of FIG. 9A.

FIG. 10 is a top view of an example of a single hole 230 having a triangular shape that may be associated with the tissue interface of FIG. 9A. For reference, the hole 230 may have an X-axis 415 extending through the centroid 405 parallel to the first orientation line 305, and a Y-axis 420 extending through the centroid 405 parallel to the second orientation line 310. If a length of the line segment 425 on the Y-axis 420 is 1.1 mm and the length of the line segment 430 on the X-axis is 1.0 mm, the perforation shape factor (PSF) would be 1.1/1.0 or about 1.1.

Figure 11A:
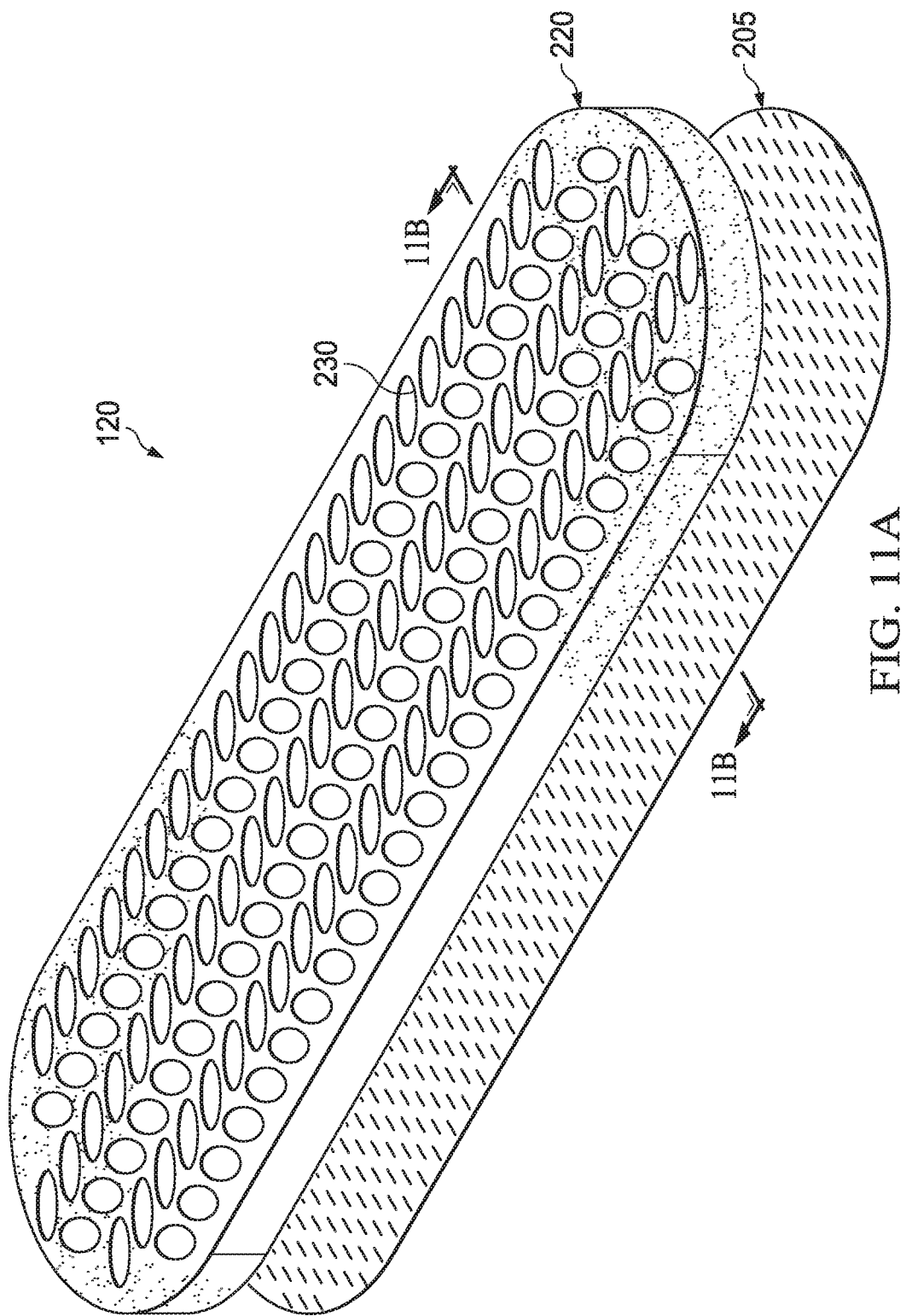
FIG. 11A is an exploded view of another example of a tissue interface that can be associated with some embodiments of the therapy system of FIG. 1.

FIG. 11A is an exploded view of an example of the tissue interface 120 of FIG. 1, illustrating additional details that may be associated with some embodiments in which the tissue interface 120 includes more than one layer. In the example of FIG. 11A, the tissue interface 120 may include the contact layer 205 and the manifold layer 210, wherein the manifold layer 210 includes the second manifold layer 220.

FIG. 11B is a cross-sectional view of the assembled tissue interface 120 of FIG. 11A along line 11B-11B. As shown in FIG. 11B, the tissue interface 120 may include the contact layer 205 and the second manifold layer 220. In some embodiments, the contact layer 205 may be coupled directly to the second manifold layer 220. For example, the contact layer 205 may be coupled to the second manifold layer 220 during the felting process. As further shown in the example of FIG. 11B, the hole depth $D_H$ of the plurality of holes 230 may be less than the thickness $T_2$ of the second manifold layer 220. Thus, the hole depth $D_H$ of the plurality of holes 230 extends partially into the thickness $T_2$ of the second manifold layer 220 from the second side 255. For example, in some embodiments, hole depth $D_H$ of the plurality of holes 230 may be less than about 95% of the thickness $T_2$ of the second manifold layer 220. In some embodiments, hole depth $D_H$ of the plurality of holes 230 may be less than about 75% of the thickness $T_2$ of the second manifold layer 220.

In some embodiments, hole depth $D_H$ of the plurality of holes 230 may be less than about 50% of the thickness $T_2$ of the second manifold layer 220.

Figure 12:
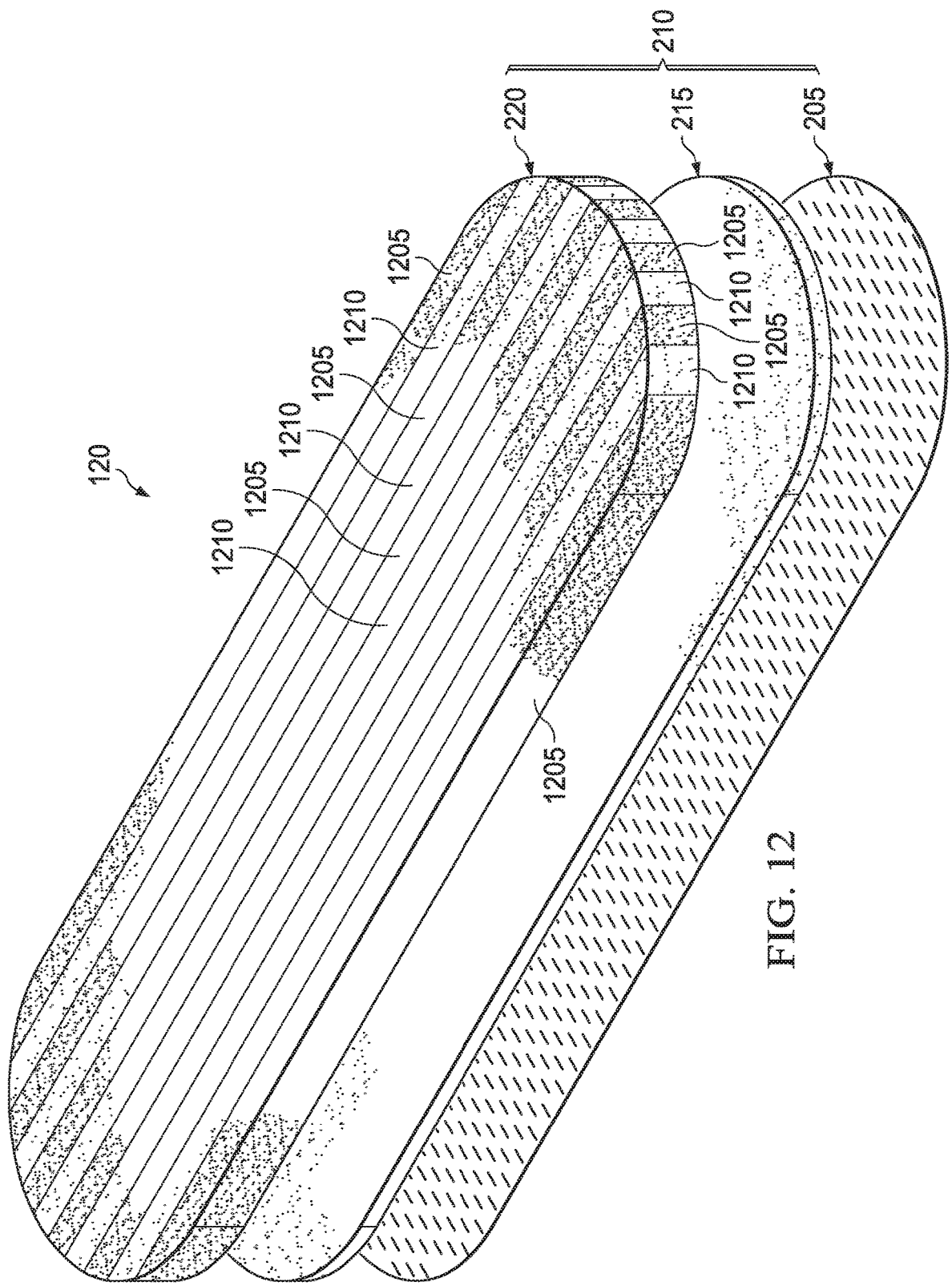
FIG. 12 is an exploded view of another example of a tissue interface that can be associated with some embodiments of the therapy system of FIG. 1.

FIG. 12 is an exploded view of an example of the tissue interface 120 of FIG. 1, illustrating additional details that may be associated with some embodiments in which the tissue interface 120 includes more than one layer. In some embodiments, the second manifold layer 220 may include a plurality of first regions 1205 having a first density and a plurality of second regions 1210 having a second density. In some embodiments, the plurality of first regions 1205 and the plurality of second regions 1210 may extend parallel to the length $L_{TI}$ of the tissue interface 120. In some embodiments, the plurality of first regions 1205 and the plurality of second regions 1210 may extend parallel to the width $W_{TI}$ of the tissue interface 120. In some embodiments, the plurality of first regions 1205 and the plurality of second regions 1210 may extend at an angle with respect to the length $L_{TI}$ of the tissue interface 120. In some embodiments, the tissue interface 120 may be oriented on a tissue site, such as a linear wound, so that the plurality of first regions 1205 and the plurality of second regions 1210 may extend parallel to the linear wound. In some embodiments, the first density may be greater than the second density. In some embodiments, the first density may be in a range from about 2 times to about 5 times greater than the second density. In some embodiments, the plurality of first regions 1205 may be formed by felting portions of the second manifold layer 220. For example, the plurality of first regions 1205 may be a felted foam having a firmness factor of about 5, and the plurality of second regions 1210 may be an unfelted foam. In some embodiments, the plurality of first regions 1205 may have a free volume in a range of about 18% to about 45%, a density in a range of about 2.6 to about 8.0 lb/ft$^3$, about 80 to about 250 pores per inch on average (e.g., as measured in the direction of compression), an average pore size in a range of about 80 to about 300 microns (e.g., as measured in the direction of compression), and/or a 25% compression load deflection of about 0.7 to about 1.75 pounds per square inch and a 65% compression load deflection of about 0.86 to about 2.15 pounds per square inch. In some embodiments, the plurality of second regions 1210 may have a free volume in a range of about 90%, a density of about 1.3 lb/ft$^3$, about 40 to about 50 pores per inch on average, an average pore size in a range of about 400 to about 600 microns, and/or a 25% compression load deflection of about 0.35 pounds per square inch and a 65% compression load deflection of about 0.43 pounds per square inch.

Generally, the plurality of second regions 1210 may be more compressible than the plurality of first regions 1205. If the tissue interface 120 is placed under a negative-pressure, the plurality of second regions 1210 may collapse before the plurality of first regions 1205. In some embodiments, if the plurality of second regions 1210 collapse, the tissue interface 120 may compress perpendicular to the plurality of second regions 1210.

FIG. 13A is a bottom view of an example of the tissue interface 120, illustrating additional details of the contact layer 205 that may be associated with some embodiments. FIG. 13B detail view of the tissue interface 120 taken at reference FIG. 13B in FIG. 13A. As illustrated in the example of FIG. 13A and FIG. 13B, the perforations 225 may each consist essentially of one or more linear slots having a length $L_P$ and a width $W_P$, wherein the length $L_P$ extends parallel to the width $W_{TI}$ of the tissue interface 120 and the width $W_P$ extends parallel to the length $L_{TI}$ of the tissue interface 120. As shown in the FIG. 13, in some embodiments, the length $L_P$ may extend parallel to the second orientation line 310, wherein the second orientation line 310 may be the primary contraction axis. A length $L_P$ of about 3 millimeters may be suitable for some examples. A width $W_P$ of about 1 millimeter or less may be suitable for some examples. FIG. 13A additionally illustrates an example of a uniform distribution pattern of the perforations 225. In FIG. 13A, the perforations 225 are substantially coextensive with the contact layer 205, and are distributed across the contact layer 205 in a grid of parallel rows and columns, in which the slots are also mutually parallel to each other. The rows may be spaced a distance $D_1$, and the perforations 225 within each of the rows may be spaced a distance $D_2$. For example, a distance $D_1$ of about 3 millimeters on center and a distance $D_2$ of about 3 millimeters on center may be suitable for some embodiments. The perforations 225 in adjacent rows may be aligned or offset. For example, adjacent rows may be offset, as illustrated in FIG. 13A, so that the perforations 225 are aligned in alternating rows separated by a distance $D_3$. A distance $D_3$ of about 6 millimeters may be suitable for some examples. The spacing of the perforations 225 may vary in some embodiments to increase the density of the perforations 225 according to therapeutic requirements.

Figure 14:
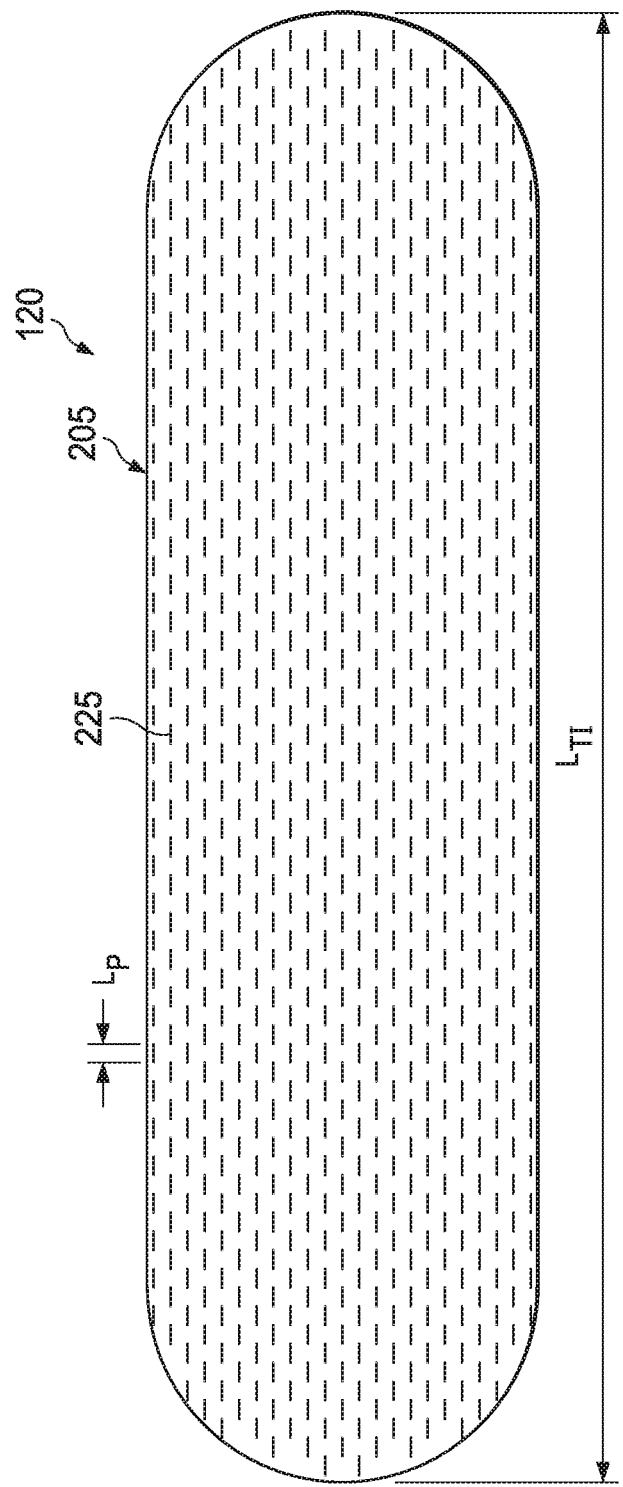
FIG. 14 is a bottom view of an example of a tissue interface that can be associated with some embodiments of the therapy system of FIG. 1.

FIG. 14 is a bottom view of another example of the tissue interface 120, illustrating additional details of the contact layer 205 that may be associated with some embodiments. As shown in FIG. 14, in some embodiments, the perforations 225 may each consist essentially of one or more linear slots having a length $L_P$ extending parallel to the length $L_{TI}$ of the tissue interface 120.

In some embodiments, one or more of the components of the dressing 110 may additionally be treated with an antimicrobial agent. For example, the manifold layer 210 may be a foam, mesh, or non-woven coated with an antimicrobial agent. In some embodiments, the manifold layer 210 may include antimicrobial elements, such as fibers coated with an antimicrobial agent. Additionally or alternatively, some embodiments of the contact layer 205 may be a polymer coated or mixed with an antimicrobial agent. In other examples, the fluid conductor may additionally or alternatively be treated with one or more antimicrobial agents. Suitable antimicrobial agents may include, for example, metallic silver, PHMB, iodine or its complexes and mixes such as povidone iodine, copper metal compounds, chlorhexidine, or some combination of these materials.

Additionally or alternatively, one or more of the components may be coated with a mixture that may include citric acid and collagen, which can reduce bio-films and infections. For example, the manifold layer 210 may be foam coated with such a mixture.

The cover 125, the contact layer 205, the manifold layer 210, or various combinations may be assembled before application or in situ. For example, the contact layer 205 may be laminated to the manifold layer 210 in some embodiments. In some embodiments, one or more layers of the tissue interface 120 may coextensive. For example, the contact layer 205 and the manifold layer 210 may be cut flush with the edge of the cover 125, exposing the edge of the manifold layer 210. In other embodiments, the contact layer 205 may overlap the edge of the manifold layer 210.

Figure 15:
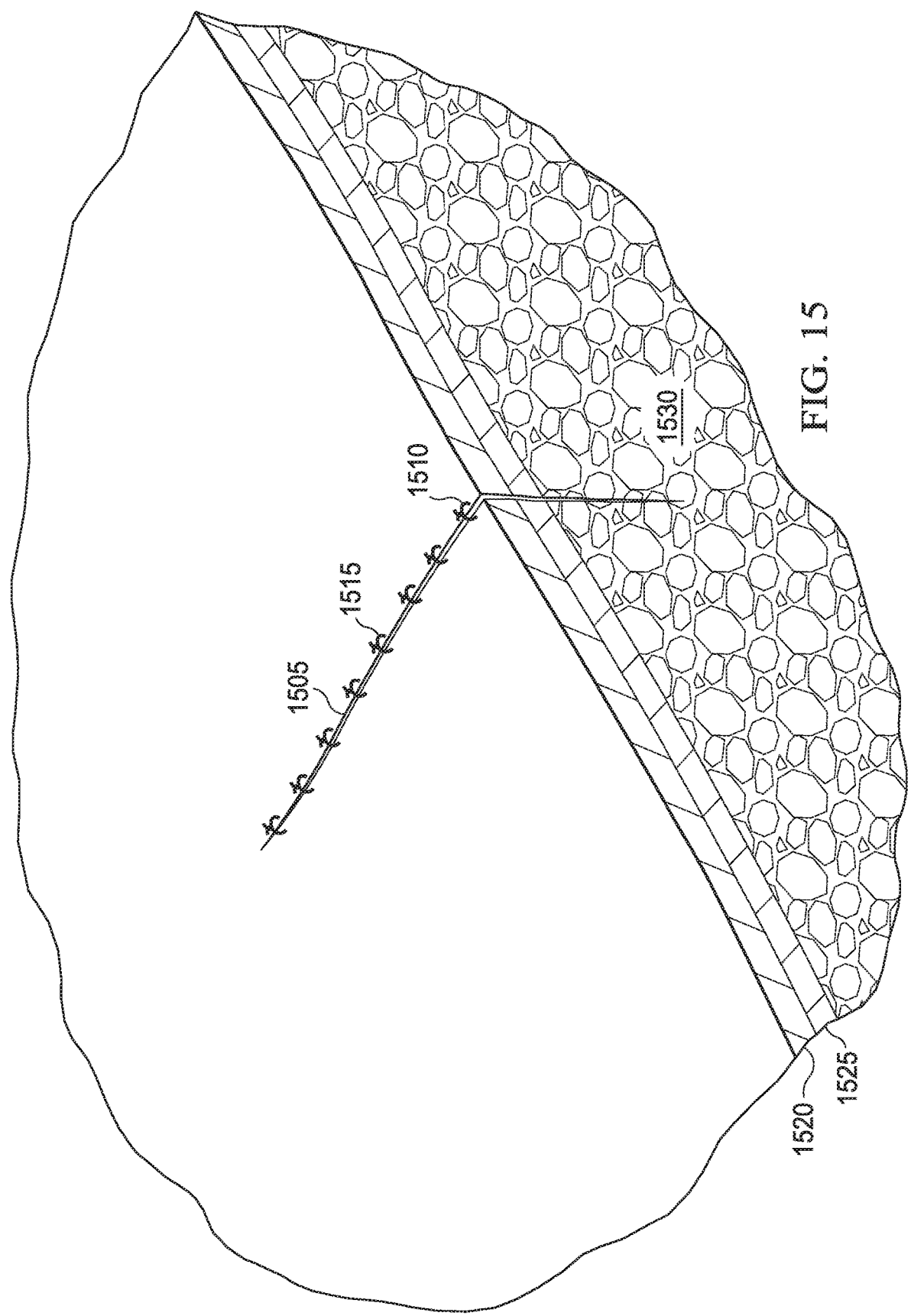
FIG. 15 is an isometric view, with a portion shown in cross-section, of a linear wound.
Figure 16:
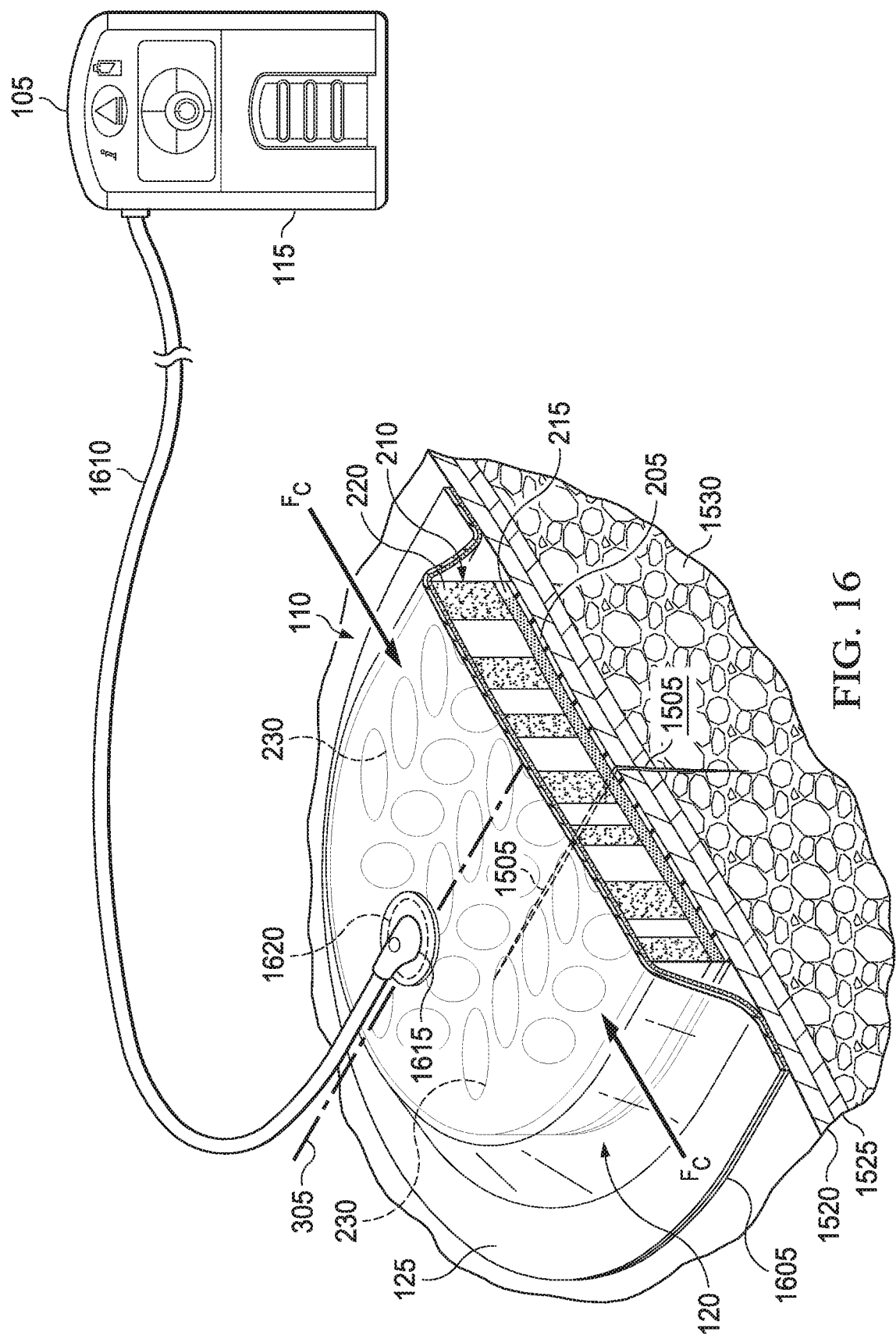
FIG. 16 is an isometric view, with a portion shown in cross-section, of a portion of an example embodiment of a therapy system being deployed over a linear wound.

Referring now primarily to FIG. 15 and FIG. 16, presented is another illustrative embodiment of a portion of the therapy system 100. FIG. 15 and FIG. 16 depict the therapy system 100 assembled in stages at a tissue site, such as a linear wound 1505. For example, the linear wound 1505 may have an elongated shape, such as an incision having a length substantially greater than its width. An incision may have edges that may be substantially parallel, particularly if the incision is caused by a scalpel, knife, razor, or other sharp blade. Other examples of a linear wound 1505 may include a laceration, a puncture, or other separation of tissue, which may have been caused by trauma, surgery, or degeneration. In some embodiments, a linear wound 1505 may also be an incision in an organ adjacent a fistula. In some embodiments, a linear wound 1505 may be an incision or puncture in otherwise healthy tissue that extends up to 40 cm or more in length. In some embodiments, a linear wound 1505 may also vary in depth. For example, an incision may have a depth that extends up to 15 cm or more or may be subcutaneous depending on the type of tissue and the cause of the incision. Additionally shown in FIG. 15, a closure device 1510, such as, for example, stitches 1515, close the linear wound 1505. Other closure devices 1510, such as epoxy or staples may be utilized to close the linear wound 1505. In some embodiments, the linear wound 1505 may be a closed incisional wound. The linear wound 1505 may include a portion through an epidermis 1520, dermis 1525, and subcutaneous tissue 1530 of a patient.

Referring now to FIG. 16, after the linear wound 1505 is closed or prepared as described above, the dressing 110 may be disposed proximate to the linear wound 1505. The geometry and dimensions of the tissue interface 120, the cover 125, or both may vary to suit a particular application or anatomy. For example, the dressing 110 may be cut to size for a specific region or anatomical area, such as for amputations. The dressing 110 may be cut without losing pieces of the tissue interface 120 and without separation of the tissue interface 120.

The tissue interface 120 can be placed over, on, or otherwise proximate to the linear wound 1505. In the example of FIG. 16, the contact layer 205 forms an outer surface of the dressing 110, and can be placed over the tissue site, including the linear wound 1505 and epidermis 1520. The contact layer 205 may be interposed between the manifold layer 210 and the tissue site, which can prevent direct contact between the manifold layer 210 and the linear wound 1505 and epidermis 1520. In some embodiments, the first manifold layer 215 can prevent direct contact between the holes 230 in the second manifold layer 220 and the linear wound 1505 and epidermis 1520. In some embodiments, the tissue interface 120 may be placed over, on, or otherwise proximate to the linear wound such that the first orientation line 305 is oriented substantially parallel to the linear wound 1505. In some embodiments, the length $L_{TI}$ of the tissue interface 120 may be oriented substantially parallel to the linear wound 1505.

In some examples, the dressing 110 may include one or more attachment devices. In some embodiments, one or more of the attachment devices may include an adhesive 1605. In some examples the adhesive 1605 may be, for example, a medically-acceptable, pressure-sensitive adhesive that extends about a periphery, a portion, or an entire surface of each of the cover 125. In some embodiments, for example, the adhesive 1605 may be an acrylic adhesive having a coating weight between 25-65 grams per square meter (g.s.m.). Thicker adhesives, or combinations of adhesives, may be applied in some embodiments to improve the seal and reduce leaks. In some embodiments, such a layer of the adhesive 1605 may be continuous or discontinuous. Discontinuities in the adhesive 1605 may be provided by apertures or holes (not shown) in the adhesive 1605. The apertures or holes in the adhesive 1605 may be formed after application of the adhesive 1605 or by coating the adhesive 1605 in patterns on a carrier layer, such as, for example, a side of the cover 125. Apertures or holes in the adhesive 1605 may also be sized to enhance the MVTR of the adhesive 1605 in some example embodiments The adhesive 1605 can be disposed on a bottom side of the cover 125, and the adhesive 1605 may pressed onto the cover 125 and epidermis 1520 (or other attachment surface) to fix the dressing 110 in position and to seal the tissue interface 120 over the patient. In some embodiments, the adhesive 1605 can be disposed only around edges of the cover 125.

FIG. 16 also illustrates one example of a fluid conductor 1610 and a dressing interface 1615. As shown in the example of FIG. 16, the fluid conductor 1610 may be a flexible tube, which can be fluidly coupled on one end to the dressing interface 1615. The dressing interface 1615 may be an elbow connector. In some examples, the tissue interface 120 can be applied to the tissue site before the cover 125 is applied over the tissue interface 120. The cover 125 may include an aperture 1620, or the aperture 1620 may be cut into the cover 125 before or after positioning the cover 125 over the tissue interface 120. The position of the aperture 1620 may be off-center or adjacent to an end or edge of the cover 125. In other examples, the aperture 1620 may be centrally disposed. The dressing interface 1615 can be placed over the aperture 1620 to provide a fluid path between the fluid conductor 1610 and the tissue interface 120. In other examples, the fluid conductor 1610 may be inserted directly through the cover 125 into the tissue interface 120.

If not already configured, the dressing interface 1615 may be disposed over the aperture 1620 and attached to the cover 125. The fluid conductor 1610 may be fluidly coupled to the dressing interface 1615 and to the negative-pressure source 105.

Negative pressure from the negative-pressure source 105 can be distributed through the fluid conductor 1610 and the dressing interface 1615 to the tissue interface 120. The dressing 110 may be a bolster to aid in closing the linear wound 1505. The tissue interface 120 may contract in response to the application of negative pressure. In some embodiments, the manifold layer 210 of the tissue interface 120 is configured to anisotropically contract. For example, under an applied negative pressure, the manifold layer 210 may contract more perpendicular to the first orientation line 305 than parallel to the first orientation line 305. The tissue interface 120 and the dressing 110 may contract more in a width-wise direction than in a length-wise direction. The preferential contraction perpendicular to the first orientation line 305 by the manifold layer 210 creates the closing force $F_C$ which may act to pull the epidermis 1520 toward the linear wound 1505 aiding in closing the linear wound 1505. The closing force $F_C$ may aid in approximating or closing the subcutaneous tissue 1530 proximate the linear wound 1505.

Figure 17:
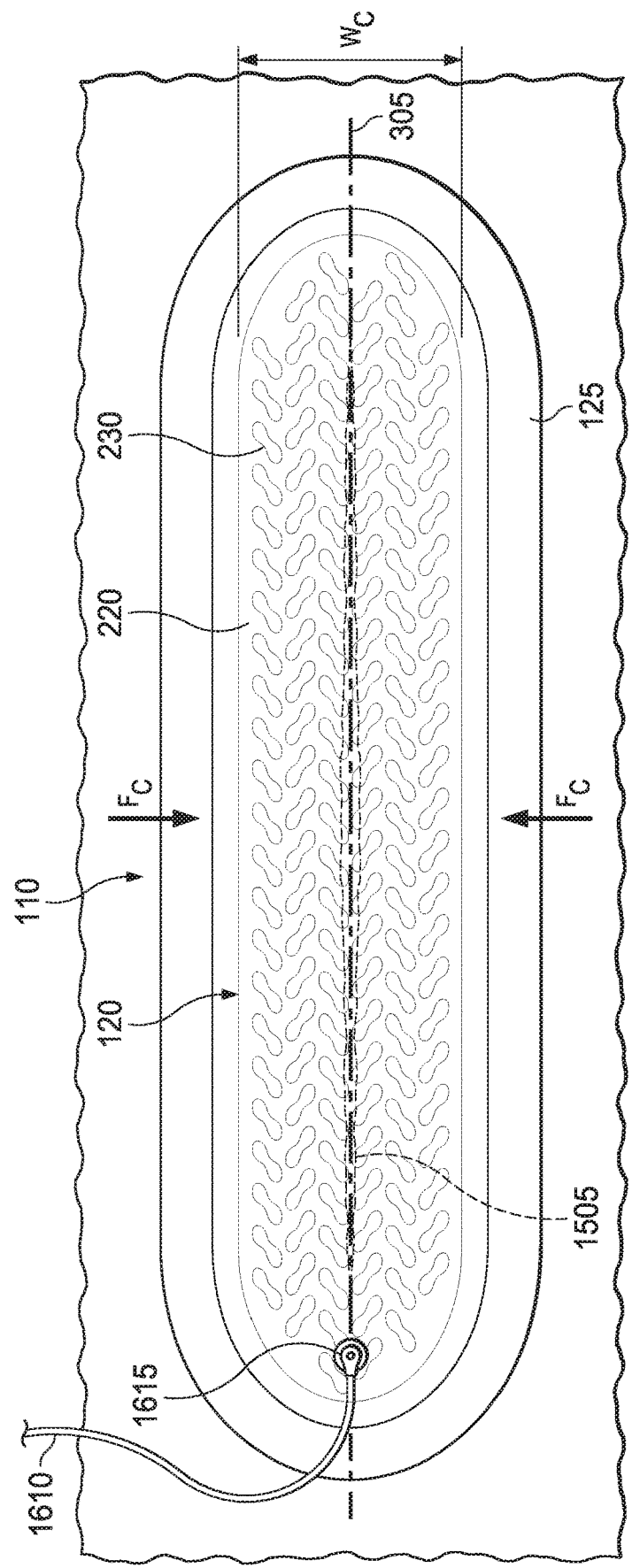
FIG. 17 is a top view of an example of a dressing under negative pressure.

FIG. 17 is a top view of an example of a dressing 110 under negative pressure, illustrating additional details that may be associated with some embodiments of the therapy system 100. The dressing 110 may have an elongate shape. The dressing 110 may have a length and a width, wherein the length is greater than the width. As shown in FIG. 17, if negative pressure is applied to the tissue interface 120, the plurality of holes 230 may collapse or contract from a relaxed position to a contracted position. The plurality of holes 230 may collapse from the relaxed position to the contracted position perpendicular to the first orientation line 305. Additionally, if negative pressure is applied to the tissue interface, and the second manifold layer 220 may collapse or contract to a contracted width, wherein the contracted width is less than a relaxed width in the absence of negative pressure. Under an applied negative pressure, the tissue interface 120 may collapse or contract, in the widthwise direction, to a contracted width $W_C$ that is less than the nominal or relaxed width $W_{TI}$ of the tissue interface 120. As the tissue interface 120 contracts perpendicular to the first orientation line 305, the contraction may be applied to the epidermis 1520 via the contact layer 205 and the cover 125. The contraction can create the closing force $F_C$. As the tissue interface 120 contracts in the widthwise direction, the dressing 110 may also contract in the widthwise direction.

Figure 18A:
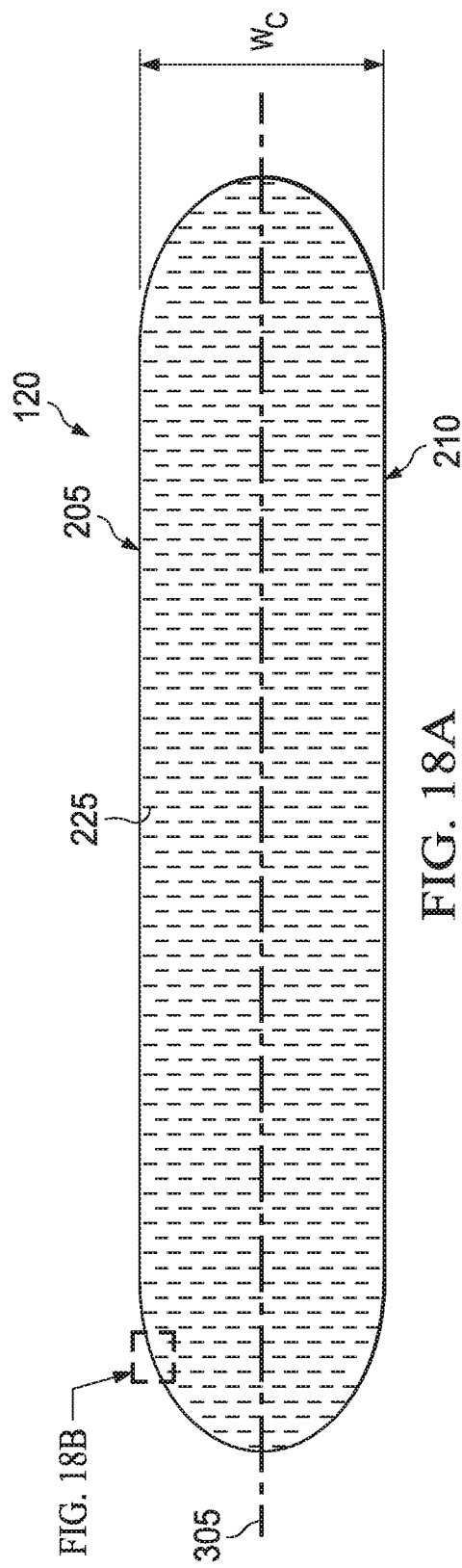
FIG. 18A is a bottom view of an example of the tissue interface of the dressing of FIG. 17.
Figure 18B:
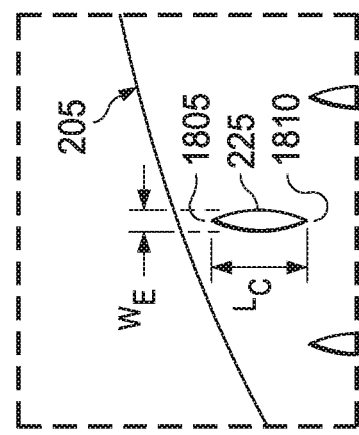
FIG. 18B is a detail view of the tissue interface taken at reference FIG. 18B in FIG. 18A.

FIG. 18A is a bottom view of the tissue interface 120 of the dressing 110 shown in FIG. 17. As shown in FIG. 18A, the tissue interface 120 is shown contracted under negative pressure. FIG. 18B is a detail view of the tissue interface taken at reference FIG. 18B in FIG. 18A. The contact layer 205 may be coupled to the manifold layer 210. Accordingly, contraction of the manifold layer 210 may be transmitted to the contact layer 205, causing the contact layer 205 to contract. The contraction of the manifold layer 210 and the contact layer 205 perpendicular to the first orientation line 305 may cause the perforations 225 to open. For example, as shown in FIG. 18B, each perforation 225 may have a first end 1805 and a second end 1810, wherein under the application of negative pressure, the contraction of the tissue interface 120 can move the first end 1805 toward the second end 1810 resulting in the perforations 225 having an expanded width $W_E$ and a contracted length $L_C$, wherein the expanded width $W_E$ is greater than the nominal width $W_P$ of the perforation 225 and the contracted length $L_C$ is less than the nominal length $L_P$ of the perforation 225. As the tissue interface 120 and the dressing 110 contract in the width-wise direction the perforations 225 may open. Opening the perforations 225 can allow liquid movement through the perforations 225 into the manifold layer 210. For example, the open perforations 225 may remove moisture from the epidermis 1520 around the linear wound 1505, which may keep the epidermis 1520 cool and/or dry. In some embodiments, negative pressure applied through the tissue interface 120 can also create a negative pressure differential across the perforations 225 in the contact layer 205, which may aid in opening or expanding the perforations 225. For example, in some embodiments in which the perforations 225 may comprise substantially closed fenestrations through the contact layer 205, a pressure gradient across the fenestrations can strain the adjacent material of the contact layer 205 and increase the dimensions of the fenestrations to allow liquid movement through them, similar to the operation of a duckbill valve.

The contact layer 205 can protect the epidermis 1520 from irritation that could be caused by expansion, contraction, or other movement of the manifold layer 210. The contact layer 205 can also substantially reduce or prevent exposure of a tissue site to the manifold layer 210, which can inhibit growth of tissue into the manifold layer 210. In some embodiments, the contact layer 205 may also The systems, apparatuses, and methods described herein may provide significant advantages. The plurality of holes 230 in the manifold layer 210 may be blind in that they do not extend all the way to the contact layer 205. A typical thin film contact layer may be ineffective at preventing the epidermis 1520 from being drawn into the plurality of holes 230. Accordingly, providing the first manifold layer 215 between the contact layer 205 and the plurality of holes 230 in the second manifold layer 220 and/or providing a plurality of holes 230 that do not extend all the way through the second manifold layer 220, provides a buffer layer between the epidermis 1520 and the plurality of holes 230. Because the plurality of holes 230 are blind, the epidermis 1520 proximate the linear wound 1505 is less likely to be drawn toward and/or into the plurality of holes 230, resulting in a reduced likelihood of the formation of tissue puckering and macro columns, such as nodules in the epidermis 1520. Puckering of the epidermis 1520 can result in a plurality of bruises and/or blisters having the same pattern as the plurality of holes. The bruises and/or blisters can be unsightly and may result in discomfort. Accordingly, because the plurality of holes 230 do not touch the contact layer 205, bruises and/or blisters and any discomfort therefrom can be reduced or eliminated.

The felted construction of the first manifold layer 215 and/or the second manifold layer 220 allows for the manifold layer 210 to be reduced in thickness while still providing good manifolding. For example, in some embodiments, the manifold layer 210 may be about 6 millimeters thick. The thin manifold layer 210 may reduce the overall thickness of the dressing 110. In some embodiments, the dressing 110 may be about 3 to 5 times thinner than other dressings. The thin dressing 110 reduces bulk and may be easy to apply, especially around difficult geometry and anatomy. Some embodiments of the tissue interface 120 may be easily cut to size to fit the tissue site and may be sealed using a single cover 125. Embodiments of the thin dressing 110 may reduce or eliminate the occurrence of leaks, reducing power usage of the negative-pressure source 105. This may be especially beneficial for battery-operated negative-pressure sources 105. Additionally, in some embodiments, smaller negative-pressure sources 105 may be used with the dressing 110, wherein such smaller negative-pressure sources 105 may be quieter or silent and may be more discrete. The lower profile dressing 110 may therefore be easy to apply around difficult anatomy, ensuring a good seal, while providing high levels of apposition or closing forces, bolstering effect, and a sterile barrier to potential infection.

The thin dressing 110 may also be more comfortable for the patient. The reduced thickness may reduce or eliminate a "tent area" that can occur between the cover 125 and the tissue interface 120, thereby reducing or eliminating skin irritation and/or hyperpigmentation around the dressing 110.

Antimicrobial agents in the dressing 110 may extend the usable life of the dressing 110 by reducing or eliminating infection risks that may be associated with extended use, particularly use with infected or highly exuding wounds.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be separated from other components for manufacture or sale. In other example configurations, the controller 130 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site, comprising;
   a manifold layer comprising a single layer of foam having a first side configured to face the tissue site, a second side opposite the first side, and a thickness between the first side and the second side, the manifold layer further comprising a plurality of holes extending into the manifold layer on the second side and having a hole depth measured from the second side, wherein the hole depth of the plurality of holes extends partially into the thickness of the manifold layer from the second side; and
   a contact layer configured to be positioned between the manifold layer and the tissue site and comprising a plurality of perforations disposed through opposing surfaces of the contact layer.

2. The dressing of claim 1, wherein the contact layer comprises a polymer film.

3. The dressing of claim 1, wherein the plurality of perforations have a perforation length and a perforation width that is shorter than and perpendicular to the perforation length, wherein the perforation length has a first end and a second end opposite the first end, and wherein the perforation width is configured to expand when a contracting force moves the first end of the perforation length closer to the second end of the perforation length.

4. The dressing of claim 1, wherein the manifold layer comprises foam having a density between about 2.6 to about 8.0 lb/ft$^3$ and a free volume in a range of about 18% to about 45%.

5. The dressing of claim 1, wherein the manifold layer has a thickness between about 3 millimeters to about 9 millimeters.

6. The dressing of claim 1, wherein the plurality of holes includes an elongate length greater than a width perpendicular to the elongate length, and wherein the elongate length of the plurality of holes is positioned at an angle relative to a longitudinal length of the manifold layer.

7. The dressing of claim 1, wherein the manifold layer comprises foam having a plurality of first regions having a first density and a plurality of second regions having a second density less than the first density.

8. The dressing of claim 1, wherein the manifold layer and the contact layer are coextensive with one another.

9. A dressing for treating a tissue site with negative pressure, the dressing comprising:
   a contact layer comprising a polymer film including a plurality of perforations through the polymer film that are configured to open;
   a first manifold layer coupled to the contact layer, the first manifold layer comprising foam having a first density; and
   a second manifold layer coupled to the first manifold layer, the second manifold layer comprising foam having a second density that is greater than the first density, the second density between about 2.6 to about 8.0 lb/ft$^3$, the second manifold layer having a first surface and a second surface including a plurality of holes extending therebetween, wherein the plurality of holes are configured to collapse from a relaxed position to a contracted position in response to an application of negative pressure to the dressing.

10. The dressing of claim 9, wherein each of the plurality of holes is adapted to collapse from the relaxed position to the contracted position perpendicular to a line of symmetry of the second manifold layer.

11. The dressing of claim 9, wherein the second manifold layer has a thickness of about 3 to about 9 mm.

12. The dressing of claim 9, wherein the foam of the second manifold layer has a 25% compression load deflection in a range of about 1.05 to about 1.75 pounds per square inch and a 65% compression load deflection in a range of about 1.29 to about 2.15 pounds per square inch.

13. The dressing of claim 9, wherein the foam of the second manifold layer comprises felted foam with a firmness factor of 3-5.

14. The dressing of claim 9, wherein each of the plurality of holes includes a perforation shape factor, wherein the perforation shape factor is a ratio of one half a first maximum length of a hole of the plurality of holes that is parallel to a desired direction of contraction to one half a second maximum length of the hole of the plurality of holes that is perpendicular to the desired direction of contraction.

15. The dressing of claim 9, wherein the contact layer is configured to contact the tissue site, the first manifold layer is in contact with the contact layer, and the second manifold layer is in contact with the first manifold layer opposite the contact layer.

16. A dressing for treating a tissue site with negative pressure, the dressing comprising:
  a contact layer configured to contact the tissue site, the contact layer comprising a polymer film;
  a first manifold coupled to the contact layer, the first manifold comprising foam; and
  a second manifold coupled to the first manifold opposite the contact layer, the second manifold comprising foam having a plurality of first regions having a first density and a plurality of second regions having a second density less than the first density;
  wherein the contact layer is configured to be between the tissue site and the first manifold when the dressing is applied to the tissue site.

17. The dressing of claim 16, wherein the second manifold has a first length and a first width, and wherein the plurality of first regions and the plurality of second regions extend parallel to the first length.

18. The dressing of claim 17, wherein the second manifold is configured to contract to a second width in response to an application of negative pressure to the second manifold, wherein the second width is less than the first width.

19. The dressing of claim 16, wherein the first density is in a range of about 2.6 to about 8.0 $lb/ft^3$.

* * * * *